United States Patent
Geuijen et al.

(10) Patent No.: US 11,753,470 B2
(45) Date of Patent: Sep. 12, 2023

(54) BISPECIFIC ANTI PD1-ANTI TIM3 ANTIBODIES

(71) Applicant: Merus N.V., Utrecht (NL)

(72) Inventors: Cecilia Anna Wilhelmina Geuijen, Utrecht (NL); Rinse Klooster, Utrecht (NL); Cornelis Adriaan De Kruif, Utrecht (NL); Paulus Johannes Tacken, Utrecht (NL); Mark Throsby, Utrecht (NL); Ton Logtenberg, Utrecht (NL)

(*) Notice: Subject to any disclaimer, the term of this patent is extended or adjusted under 35 U.S.C. 154(b) by 593 days.

(21) Appl. No.: 16/628,937

(22) PCT Filed: Jul. 6, 2018

(86) PCT No.: PCT/NL2018/050450
§ 371 (c)(1),
(2) Date: Jan. 6, 2020

(87) PCT Pub. No.: WO2019/009727
PCT Pub. Date: Jan. 10, 2019

(65) Prior Publication Data
US 2020/0216539 A1    Jul. 9, 2020

(30) Foreign Application Priority Data

Jul. 6, 2017 (EP) .................... 17180061

(51) Int. Cl.
*C07K 16/28* (2006.01)
(52) U.S. Cl.
CPC ...... *C07K 16/2818* (2013.01); *C07K 2317/31* (2013.01); *C07K 2317/52* (2013.01); *C07K 2317/565* (2013.01); *C07K 2317/76* (2013.01)
(58) Field of Classification Search
None
See application file for complete search history.

(56) References Cited

U.S. PATENT DOCUMENTS

| | | |
|---|---|---|
| 9,248,181 B2 | 2/2016 | De Kruif et al. |
| 9,358,286 B2 | 6/2016 | De Kruif et al. |
| 2003/0078385 A1 | 4/2003 | Arathoon et al. |
| 2017/0037145 A1 | 2/2017 | Geuijen et al. |

FOREIGN PATENT DOCUMENTS

| | | | |
|---|---|---|---|
| JP | 2015532278 A | 11/2015 | |
| WO | WO 2004009618 A2 | 1/2004 | |
| WO | WO 2009126920 A2 | 10/2009 | |
| WO | WO 2009157771 A1 | 12/2009 | |
| WO | WO-2011159877 A2 * | 12/2011 | ............ A61P 31/00 |
| WO | WO 2013157953 A1 | 10/2013 | |
| WO | WO 2013157954 A1 | 10/2013 | |
| WO | WO-2014051433 A1 | 4/2014 | |
| WO | WO 2017055399 A1 | 4/2017 | |
| WO | WO-2017055404 A1 * | 4/2017 | ....... A61K 39/39533 |
| WO | WO 2017055404 A1 | 4/2017 | |
| WO | WO 2017069628 A2 | 4/2017 | |
| WO | WO-2017079116 A2 | 5/2017 | |

OTHER PUBLICATIONS

Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Lescar, et al. Journal of Biological Chemistry 270.30 (1995): 18067-18076.*
Kanyavuz et al., Nat Rev Immunol. Jun. 2019;19(6):355-368. doi: 10.1038/S41577-019-0126-7.*
Almagro, J.C. and Fransson, J., "Humanization of antibodies," *Frontiers in Bioscience* 13:1619-1633, Frontiers in Bioscience, United States (2008).
Anonymous, "Preliminary prospectus, MERUS U.S. Pat. No. 4,333,333 Shares Merus B.V. Common Shares," United States Securities and Exchange Commission, 215 pages, (2016), available at: https://www.sec.gov/Archives/edgar/data/1651311/000119312516582683/d29248dfla.htm.
Armour, K.L. et al., "Recombinant human IgG molecules lacking Fc gamma receptor I binding and monocyte triggering activities," *Eur. J. Immunol.* 29(8):2613-24, Wiley-VCH Verlag, Germany (1999).
De Haard, H.J. et al., "A large non-immunized human Fab fragment phage library that permits rapid isolation and kinetic analysis of high affinity antibodies," *J. Biol. Chem.* 274(26):18218-18230, American Society for Biochemistry and Molecular Biology, Inc., United States (1999).

(Continued)

*Primary Examiner* — Michael Szperka
(74) *Attorney, Agent, or Firm* — STERNE, KESSLER, GOLDSTEIN & FOX P.L.L.C.; Paul Calvo

(57) ABSTRACT

The disclosure provides means and methods for interfering with Programmed Cell Death 1 protein (PD-1) and T-cell immunoglobulin and mucin-domain containing-3 (TIM-3) mediated inhibition in a PD-1 and/or TIM-3 positive cell. A method may comprise contacting said cell with an antibody or a functional part, derivative and/or analogue thereof that comprises a variable domain that can bind to an extracellular part of PD-1 and a variable domain that can bind to an extracellular part of TIM-3, thereby inhibiting PD-1 and/or TIM-3 mediated activity in said cell. The invention also provides antibodies or variants thereof that comprises a variable domain that can bind to an extracellular part of PD-1 and a variable domain that can bind to an extracellular part of TIM-3.

14 Claims, 16 Drawing Sheets
Specification includes a Sequence Listing.

(56) References Cited

OTHER PUBLICATIONS

Idusogie, E.E., et al., "Mapping of the C1q Binding Site on Rituxan, a chimeric Antibody with a Human IgG1 Fc," *J Immunol.* 164(8):4178-84, American Association of Immunologists, United States (2000).

International Search Report and Written Opinion for Application No. PCT/NL2018/050450, dated Oct. 16, 2018, European Patent Office, Rijswijk, 15 pages.

Labrijn, A., et al., "Therapeutic IgG4 antibodies engage in Fab-arm exchange with endogenous human IgG4 in vivo," *Nat Biotechnol.* 27(8):161-71, Nature Publishing Group, Great Britain (2009).

Marks, J.D., et al., "By-passing immunization. Human antibodies from V-gene libraries displayed on phage," *J Mol Biol.* 222(3):581-97, Academic Press Limited, United States (1991).

Morrison, S.L. "Two heads are better than one," *Nature Biotechnol.* 25(11):1233-1234, Nature Publishing Group, Great Britain (2007).

Shields, R.L., et al., "High resolution mapping of the binding site on human IgG1 for Fc gamma RI, Fc gamma RII, Fc gamma RIII, and FcRn and design of IgG1 variants with improved binding to the Fc gamma R," *J Biol Chem.* 276(9):6591-604, The American Society for Biochemistry and Molecular Biology, Inc., United States (2001).

Duraiswamy, J., et al., "Therapeutic PD-1 Pathway Blockade Augments With Other Modalities of Immunotherapy T-cell Function to Prevent Immune Decline in Ovarian Cancer," Cancer Research 73(23):6900-6912, American Association for Cancer Research, United States (Dec. 2013).

Marwick, L.J.L., et al., "Blockade of PD1 and TIM3 restores innate and adaptive immunity in patients with acute alcoholic hepatitis," Gastroenterology 148(3): 590-602, Elsevier, Netherlands (2015).

\* cited by examiner

DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIK
RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC  (SEQ ID NO: 24)

Figure 1B

```
gacatccagatgacccagtctccatcctccctgtctgcatctgtaggagacagagtcacc
 D   I   Q   M   T   Q   S   P   S   S   L   S   A   S   V   G   D   R   V   T
atcacttgccgggcaagtcagagcattagcagctacttaaattggtatcagcagaaacca
 I   T   C   R   A   S   Q   S   I   S   S   Y   L   N   W   Y   Q   Q   K   P
gggaaagcccctaagctcctgatctatgctgcatccagtttgcaaagtggggtcccatca
 G   K   A   P   K   L   L   I   Y   A   A   S   S   L   Q   S   G   V   P   S
aggttcagtggcagtggatctgggacagatttcactctcaccatcagcagtctgcaacct
 R   F   S   G   S   G   T   D   F   T   L   T   I   S   S   L   Q   P
gaagattttgcaacttactactgtcaacagagttacagtacccctccaacgttcggccaa
 E   D   F   A   T   Y   Y   C   Q   Q   S   Y   S   T   P   P   T   F   G   Q
gggaccaaggtggagatcaaa  (SEQ ID NO: 25)
 G   T   K   V   E   I   K   (SEQ ID NO: 26)
```

Figure 1C

```
cgaactgtggctgcaccatctgtcttcatcttcccgccatctgatgagcagttgaaatct
 R   T   V   A   A   P   S   V   F   I   F   P   P   S   D   E   Q   L   K   S
ggaactgcctctgttgtgtgcctgctgaataacttctatcccagagaggccaaagtacag
 G   T   A   S   V   V   C   L   L   N   N   F   Y   P   R   E   A   K   V   Q
tggaaggtggataacgccctccaatcgggtaactcccaggagagtgtcacagagcaggac
 W   K   V   D   N   A   L   Q   S   G   N   S   Q   E   S   V   T   E   Q   D
agcaaggacagcacctacagcctcagcagcaccctgacgctgagcaaagcagactacgag
 S   K   D   S   T   Y   S   L   S   S   T   L   T   L   S   K   A   D   Y   E
aaacacaaagtctacgcctgcgaagtcacccatcagggcctgagctcgcccgtcacaaag
 K   H   K   V   Y   A   C   E   V   T   H   Q   G   L   S   S   P   V   T   K
agcttcaacaggggagagtgttag  (SEQ ID NO: 27)
 S   F   N   R   G   E   C   -   (SEQ ID NO: 28)
```

Figure 1D

DIQMTQSPSSLSASVGDRVTITCRASQSISSYLNWYQQKPGKAPKLLIYAASSLQSGVPSRFSGSGSG
TDFTLTISSLQPEDFATYYCQQSYSTPPITFGQGTRLEIK (SEQ ID NO: 29)

Figure 1E

DIQMTQSPSSLSASVGDRVTITCRASQSISSYLNWYQQKPGKAPKLLIYAASSLQSGVPSRFSGSGSG
TDFTLTISSLQPEDFATYYCQQSYSTP (SEQ ID NO: 30)

(underlining shows CDRs)

FIGURE 2

IgG heavy chains for the generation of bispecific molecules

Figure 2A

VH: dependent on the MF (target): Figure 3.

Figure 2B

CH1 Region:

```
gctagcaccaagggcccatcggtcttccccctggcaccctcctccaagagcacctctggg
 A   S   T   K   G   P   S   V   F   P   L   A   P   S   S   K   S   T   S   G
ggcacagcggccctgggctgcctggtcaaggactacttccccgaaccggtgacggtgtcg
 G   T   A   A   L   G   C   L   V   K   D   Y   F   P   E   P   V   T   V   S
tggaactcaggcgccctgaccagcggcgtgcacaccttcccggctgtcctacagtcctca
 W   N   S   G   A   L   T   S   G   V   H   T   F   P   A   V   L   Q   S   S
ggactctactccctcagcagcgtcgtgaccgtgccctccagcagcttgggcacccagacc
 G   L   Y   S   L   S   S   V   V   T   V   P   S   S   S   L   G   T   Q   T
tacatctgcaacgtgaatcacaagcccagcaacaccaaggtggacaagagagtt         (SEQ ID NO: 31)
 Y   I   C   N   V   N   H   K   P   S   N   T   K   V   D   K   R   V          (SEQ ID NO: 32)
```

Figure 2C

Hinge Region:

```
gagcccaaatcttgtgacaaaactcacacatgcccaccgtgccca   (SEQ ID NO: 33)
 E   P   K   S   C   D   K   T   H   T   C   P   P   C   P   (SEQ ID NO: 34)
```

Figure 2D

CH2 Region:

gcacctgaactcctggggggaccgtcagtcttcctcttccccccaaaacccaaggacacc
A   P   E   L   L   G   G   P   S   V   F   L   F   P   P   K   P   K   D   T
ctcatgatctcccggacccctgaggtcacatgcgtggtggtggacgtgagccacgaagac
L   M   I   S   R   T   P   E   V   T   C   V   V   V   D   V   S   H   E   D
cctgaggtcaagttcaactggtacgtggacggcgtggaggtgcataatgccaagacaaag
P   E   V   K   F   N   W   Y   V   D   G   V   E   V   H   N   A   K   T   K
ccgcgggaggagcagtacaacagcacgtaccgtgtggtcagcgtcctcaccgtcctgcac
P   R   E   E   Q   Y   N   S   T   Y   R   V   V   S   V   L   T   V   L   H
caggactggctgaatggcaaggagtacaagtgcaaggtctccaacaaagcccctcccagcc
Q   D   W   L   N   G   K   E   Y   K   C   K   V   S   N   K   A   L   P   A
cccatcgagaaaaccatctccaaagccaaa   (SEQ ID NO: 35)
P   I   E   K   T   I   S   K   A   K   (SEQ ID NO: 36)

Figure 2E

CH2 region containing L235G and G236R silencing substitutions:

gcacctgaactcggcaggggaccgtcagtcttcctcttccccccaaaacccaaggacacc
A   P   E   L   G   R   G   P   S   V   F   L   F   P   P   K   P   K   D   T
ctcatgatctcccggacccctgaggtcacatgcgtggtggtggacgtgagccacgaagac
L   M   I   S   R   T   P   E   V   T   C   V   V   V   D   V   S   H   E   D
cctgaggtcaagttcaactggtacgtggacggcgtggaggtgcataatgccaagacaaag
P   E   V   K   F   N   W   Y   V   D   G   V   E   V   H   N   A   K   T   K
ccgcgggaggagcagtacaacagcacgtaccgtgtggtcagcgtcctcaccgtcctgcac
P   R   E   E   Q   Y   N   S   T   Y   R   V   V   S   V   L   T   V   L   H
caggactggctgaatggcaaggagtacaagtgcaaggtctccaacaaagcccctcccagcc
Q   D   W   L   N   G   K   E   Y   K   C   K   V   S   N   K   A   L   P   A
cccatcgagaaaaccatctccaaagccaaa   (SEQ ID NO: 37)
P   I   E   K   T   I   S   K   A   K   (SEQ ID NO: 38)

Figure 2F

CH3 domain containing substitutions L351K and T366K (KK)

```
gggcagccccgagaaccacaggtgtacaccaagcccccatcccgggaggagatgaccaag
 G  Q  P  R  E  P  Q  V  Y  T  K  P  P  S  R  E  E  M  T  K
aaccaggtcagcctgaagtgcctggtcaaaggcttctatcccagcgacatcgccgtggag
 N  Q  V  S  L  K  C  L  V  K  G  F  Y  P  S  D  I  A  V  E
tgggagagcaatgggcagccggagaacaactacaagaccacgcctcccgtgctggactcc
 W  E  S  N  G  Q  P  E  N  N  Y  K  T  T  P  P  V  L  D  S
gacggctccttcttcctctatagcaagctcaccgtggacaagagcaggtggcagcagggg
 D  G  S  F  F  L  Y  S  K  L  T  V  D  K  S  R  W  Q  Q  G
aacgtcttctcatgctccgtgatgcatgaggctctgcacaaccactacacgcagaagagc
 N  V  F  S  C  S  V  M  H  E  A  L  H  N  H  Y  T  Q  K  S
ctctccctgtctccgggttga   (SEQ ID NO: 39)
 L  S  L  S  P  G  -    (SEQ ID NO: 40)
```

Figure 2G

CH3 domain containing substitutions L351D and L368E (DE)

```
gggcagccccgagaaccacaggtgtacaccgacccccatcccgggaggagatgaccaag
 G  Q  P  R  E  P  Q  V  Y  T  D  P  P  S  R  E  E  M  T  K
aaccaggtcagcctgacctgcgaggtcaaaggcttctatcccagcgacatcgccgtggag
 N  Q  V  S  L  T  C  E  V  K  G  F  Y  P  S  D  I  A  V  E
tgggagagcaatgggcagccggagaacaactacaagaccacgcctcccgtgctggactcc
 W  E  S  N  G  Q  P  E  N  N  Y  K  T  T  P  P  V  L  D  S
gacggctccttcttcctctatagcaagctcaccgtggacaagagcaggtggcagcagggg
 D  G  S  F  F  L  Y  S  K  L  T  V  D  K  S  R  W  Q  Q  G
aacgtcttctcatgctccgtgatgcatgaggctctgcacaaccactacacgcagaagagc
 N  V  F  S  C  S  V  M  H  E  A  L  H  N  H  Y  T  Q  K  S
ctctccctgtctccgggttga    (SEQ ID NO: 41)
 L  S  L  S  P  G  -     (SEQ ID NO: 42)
```

FIGURE 3

Amino acid sequences of heavy chain variable regions:

Figure 3A: Heavy chain variable regions of PD-1 specific clones

MF6076

QVQLQESGPGLVKPSETLSLTCTVSTDSLGFYFWSWIRQPPGKGLEWIGYIYYSGSAN
FNPSLKSRVTMSIDTSNNQFSLKLRSVTAADTAVYFCARGGYTGYGGDWFDPWGQG
TLVTVSS (SEQ ID NO: 43)

MF6226

QVQLQESGPGLVKPSETLSLTCTVSGDSIGYYFWSWIRQPPGKGLEWIGYVYYSGSNN
LNPSLKSRVTLSVDTSKNQFSLRLNSMTAADTAVYYCARGGYSGYGGDSFDLWGQGT
TVTVSS (SEQ ID NO: 44)

MF6236

QVQLQESGPGLVKPSETLSLTCTVSGGSIGYYFWSWIRQPPGKGLEWIGYIYYSGSTN
FNPSLKSRVTMSVDTSKNQFSLNLRSVTTADTAVYYCARGGYTGHGGDWFDPWGQG
TLVTVSS (SEQ ID NO: 45)

MF6256

EVQLVQSGAEVKKPGSSMKVSCKASGGTFSSYVISWVRQAPGQGLEWMGMIIPVFDT
SSYEKKFQGRITIIADKSTSTVYLELSSLRSEDAAVYYCARGTVEATLLFDFWGQGTLV
TVSS (SEQ ID NO: 46)

MF6930

EVQLVQSGAEVKKPGSSMKVSCKASGGTFSNYVISWVRQAPGQGLEWMGMIIPVFET
ATYEKKFQGRVTIIADKSTSTVYMELSSLRSEDAAVYYCARGTVEATLLFDYWGQGTL
VTVSS (SEQ ID NO: 47)

QVQLVQSGAEVKKPGSSVKVSCKASGGTFS<u>SYAIS</u>WVRQAPGQGLEWMG<u>MIIPFFDT
ANYAQKFQG</u>RVTITADKSTSTASMELRSLRSEDTAVYYCAR<u>GTVSATLVFDY</u>WGQGT
LVTVSS (SEQ ID NO: 48)

MF6935

QVQLVQSGAEVKKPGSSVKVSCKASGGTFS<u>SYVIS</u>WVRQAPGQGLEWMG<u>MIIPIFDT
ANYAQKFQG</u>RVTITADKSTSTASMELRSLRSEDTAVYYCAR<u>GTVSGTLVFDY</u>WGQGT
LVTVSS (SEQ ID NO: 49)

MF6936

EVQLVQSGAEVKKPGSSVKVSCKASGDTFS<u>NYVIN</u>WVRQAPGQGLEWMG<u>MIIPVFDT
TSYERKFQG</u>RVTITADKSTSTAYMELTSLRSEDTAVYYCAR<u>GTVGATLLFDN</u>WGQGT
LVTVSS (SEQ ID NO: 50)

MF6972

EVQLQESGPGLVKPSETLSLTCTVSGGSIS<u>TYFWS</u>WIRQPPGKGLEWIG<u>YIIYSGSTNY
NPSLKS</u>RVTISVDTSKNQFSLKLSSVTAADTAVYYCAR<u>GGYSGYGGDDFDI</u>WGQGTM
VTVSS (SEQ ID NO: 51)

MF6974

EVQLVESGGDLVQPGGSLRLSCAASGFTFN<u>SYAMS</u>WVRQAPGKGLEWVS<u>TISGGGA
NIYYADSVKG</u>RFTISRDNSKSTLYLQMNSLRAEDTAVYFCAS<u>PYGSGYFDV</u>WGQGTL
VTVSS (SEQ ID NO: 52)

MF6982

EVQLVESGGDLVQPGGSLRLSCAASGFTFS<u>SYAMS</u>WVRQAPGKGLEWVS<u>TISGGGTN
IYYADSVKG</u>RFTISRDNSKNTLFLQMNSLRAGDTAVYYCAS<u>PYGSGYLDV</u>WGQGTLV
TVSS (SEQ ID NO: 53)

Figure 3B: Heavy chain variable regions of TIM-3 specific clones

MF7676

QITLKESGPTLVKPTQTLTLTCTFSGFSLSTSKVGVGWIRQPPGKALEWLALIYWNDD
KRYSPSLKSRLTITKDTSKNQVVLTMTNMDPVDTATYYCAHRRGWGPFDYWGQGTL
VTVSS  (SEQ ID NO: 54)

MF7677

QITLKESGPTLVKPTQTLTLTCTFSGFSLSTSGVGVGWIRQPPGKALEWLAFIYSNDD
KRYSPSLKSRLTITKDTSKNQVVLTMTNMDPVDTATYYCTHRRGWGPFDYWGQGTL
VTVSS  (SEQ ID NO: 55)

MF7678

QITLKESGPTLVKPTQTLTLTCTFSGFSLSTSGVGVGWIRQPPGKALEWLVFIYSNDD
KRYSPSLKSRLTITKDTSKNQVVLTMTNMDPVDTATYYCAHRRGWGPFDYWGQGTL
VTVSS  (SEQ ID NO: 56)

MF7679

QITLKESGPTLVKPTQTLTLTCTFSGFSLSTSGVGVGWIRQPPGKALEWLALIYWNDD
KRYSPSLKSRLTITKDTSKNQVVLTMTNMDPVDTATYYCAHRRGWGPFDYWGQGTL
VTVSS  (SEQ ID NO: 57)

(underlining shows CDRs)

FIGURE 8

EVQLVETGAEVKKPGASVKVSCKASDYIFTKYDINWVRQAPGQGLEWMGWMSANTGNTGYAQKFQGRVTMTRDTS
INTAYMELSSLTSGDTAVYFCARSSLFKTETAPYYHFALDVWGQGTTVTVSS (SEQ IDNO: 58)

BISPECIFIC ANTI PD1-ANTI TIM3 ANTIBODIES

CROSS-REFERENCE TO RELATED APPLICATIONS

This application is a U.S. national stage filing of International Application No. PCT/NL2018/050450, filed Jul. 6, 2018; which claims priority to EP Application No. 17180061.8, filed Jul. 6, 2017. The entire contents of International Application No. PCT/NL2018/050450 are hereby incorporated herein by reference.

REFERENCE TO A SEQUENCE LISTING SUBMITTED ELECTRONICALLY VIA EFS-WEB

The content of the electronically submitted sequence listing (Name: "4096_0290001_Seqlisting_ST25.txt"; Size: 66,246 bytes; and Date of Creation: Jan. 24, 2023) is herein incorporated by reference in its entirety.

The invention relates to the field of antibodies. In particular it relates to the field of therapeutic antibodies for the treatment of diseases involving aberrant cells. More in particular it relates to antibodies that bind extracellular parts of two or more membrane associated proteins and thereby modulate biological activity expressed by a cell.

Cancer is still a major cause of death in the world, in spite of the many advances that have been made in the treatment of the disease and the increased knowledge of the molecular events that lead to cancer. Colorectal cancer (CRC), for instance, is the third most common cancer worldwide. In 2008, 1.23 million people were diagnosed with the disease. It is the second most common cancer in Europe, with around 447,000 new cases diagnosed in 2012 (13% of the total). Colorectal cancer is the fourth most common cause of cancer death, estimated to be responsible for 608.000 (EU 148,000) deaths per annum. While some new treatments have been advanced in CRC many have failed clinical testing; metastatic CRC is still largely incurable with conventional treatments. Melanoma is another example of a cancer that occurs very frequently. When detection is not early enough the cancer is likely to metastasize at which stage it is very hard to treatment. Immune-intervention treatments have been shown to be effective to at least some of the patients with metastasized melanoma. Non-small cell lung cancer is a cancer type that is rarely discovered at an early enough stage for surgery. Also these types of cancers have been successfully treatment with immune-intervention treatments.

Traditionally, most cancer drug discovery has focused on agents that block essential cell functions and kill dividing cells. However, in cases of advanced cancer, no matter how aggressively applied, even to the point where patients suffer life-threatening side-effects from the treatment, chemotherapy rarely results in a complete cure. In most cases the tumors in the patients stop growing or temporarily shrink (referred to as remission) only to start proliferating again, some times more rapidly (referred to as relapse), and become increasingly more difficult to treat. More recently the focus of cancer drug development has moved away from broadly cytotoxic chemotherapy to targeted cytostatic therapies with less toxicity. Treatment of advanced cancer has been validated clinically in leukemia and some other cancers. However, in a majority of carcinomas, targeted approaches are still proving not effective enough to completely abolish cancer in the majority of the patients.

Targeting of cancers has been achieved using a variety of different methods including for instance small molecules directed towards signaling proteins on which the cancer depends for survival and/or growth; vaccines with tumor specific proteins: cell therapies with immune cells that actively kill tumor cells and antibodies that target cytotoxic molecules to the tumor; interfere with signaling and/or that (re)direct the immune system of the host to the tumor cells.

The present invention provides novel means and methods for (re)directing immune system components. The invention also relates to means and methods for modulating a biological activity expressed by cells.

SUMMARY OF THE INVENTION

The invention provides a method for interfering with Programmed Cell Death 1 protein (PD-1) and T-cell immunoglobulin and mucin-domain containing-3 (TIM-3) mediated inhibition in a PD-1 and/or TIM-3 positive cell, the method comprising contacting said cell with an antibody or a functional part, derivative and/or analogue thereof that comprises
  a variable domain that can bind to an extracellular part of PD-1 and
  a variable domain that can bind to an extracellular part of TIM-3, thereby inhibiting PD-1 and/or TIM-3 mediated activity in said cell.

The invention also provides a method for stimulating the formation, stability and/or activity of an immunological synapse comprising providing a system that comprises at least two cells capable of associating with each other via an immunological synapse and providing said system with an antibody or a functional part, derivative and/or analogue thereof that comprises
  a variable domain that can bind to an extracellular part of PD-1 and
  a variable domain that can bind to an extracellular part of TIM-3.
  thereby stimulating the formation, stability and/or activity of an immunological synapse between said at least two cells.

Further provided is an antibody or variant thereof that comprises a variable domain that can bind to an extracellular part of PD-1 and a variable domain that can bind to an extracellular part of TIM-3.

Further provided is an antibody or variant thereof that comprises a variable domain that can bind to an extracellular part of PD-1 and a variable domain that, can bind to an extracellular part of TIM-3: wherein the variable domain that can bind PD-1 comprises a heavy chain variable region with a CDR3 region that comprises the amino acid sequence of the CDR3 of a variable heavy chain region of one of the VH1 depicted for MF6076: MF6236; MF6256; MF6226: MF6930; MF6932; MF6935; MF6936; MF6972: MF6974; or MF6982; preferably MF6226; MF6256; or MF6930 in FIG. 3. In a preferred embodiment said variable domain that can bind PD-1 comprises a heavy chain variable region comprises a heavy chain variable region with a CDR1, CDR2 and CDR3 region that comprises the amino acid sequence of the CDR1, CDR2 and CDR3 of a variable heavy chain region of one of the VH depicted for MF6076; MF6236: MF6256; MF6226; MF6930: MF6932; MF6935; N6936; MF6972: MF6974; or MF6982: preferably MF6226; MF6256; or MF6930 in FIG. 3.

Further provided is an antibody or variant thereof that comprises a variable domain that can bind to an extracellular part of PD-1 and a variable domain that can bind to an extracellular part of TIM-3: wherein the variable domain that can bind PD-1 comprises a heavy chain variable region that comprises the amino acid sequence of the variable heavy chain region as depicted for MF6076; MF6256: MF6226; MF6930; MF6932: MF6935; MF6936; MF6972: MF6974; or MF6982: preferably MF6226; MF6256: or MF6930 (as depicted in FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the VI as depicted for MF.

The variable domain that can bind to an extra-cellular part of TIM-3 preferably comprises a heavy chain variable region with a CDR3 region that comprises the amino acid sequence of the CDR3 region of the variable heavy chain region as depicted for MF7676: MF7677; MF7678; or MF7679 of FIG. 3. Preferably variable domain that can bind to an extra-cellular part of TIM-3 and that comprises a heavy chain variable region with a CDR1, CDR2 and CDR3 region that comprises the amino acid sequence of the CDR1, CDR2 and CDR3 of a variable heavy chain region of one of the VII depicted for MF7676; MF7677; MF7678: or MF7679 of FIG. 3.

The variable domain that can bind to an extra-cellular part of TIM-3 preferably comprises a heavy chain variable region that comprises the amino acid sequence of the variable heavy chain region as depicted for MF7676; MF7677: MF7678; or MF7679 (of FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the indicated MF.

An antibody of the invention preferably comprises a heavy chain variable region comprising an amino acid sequence of an MF as depicted in FIG. 3. In a preferred embodiment the antibody further comprises a light chain variable region that comprises an amino acid sequence of a light chain variable region depicted in FIG. 1. In a preferred embodiment the light chain comprises an amino acid sequence as depicted in FIG. 1A. In a preferred embodiment the heavy chain comprises a constant region of an IgG1 antibody, preferably a human IgG1 antibody. In a preferred embodiment the CH2 region of said IgG1 constant region is engineered to reduce ADCC and/or CDC activity of the antibody. In a preferred embodiment the CH2 region comprises a sequence as depicted in FIG. 2E. In a preferred embodiment the CH3-region of the antibody is engineered to facilitate heterodimerization of the heavy chains. In a preferred embodiment one heavy chain comprises a sequence as depicted in FIG. 2F and another heavy chain comprises a sequence as depicted in FIG. 2G.

Further provided is a pharmaceutical composition that comprises one or more antibodies or variants thereof of the invention.

Also provided is a nucleic acid molecule or a collection of nucleic acid molecules that codes for a heavy chain(s) or a heavy chain variable region(s) of an antibody of the invention or a variant thereof.

Also provided is a nucleic acid molecule or collection of nucleic acid molecules that codes for an antibody of the invention.

Also provided is a cell comprising one or more nucleic acid molecules that alone or together code for an antibody or a variant thereof of the invention. Also provided are methods of producing an antibody or a variant thereof of the invention using a cell as described, preferably together with the harvesting of the antibody or variant thereof from a culture of the cells.

Further provided is a cell system that comprises an antibody or variant thereof of the invention.

Also provided is a method for the treatment of an individual that has a disease involving aberrant cells such as cancer or has a chronic infection with a virus or parasite, the method comprising administering an antibody or a variant thereof of the invention, preferably a bispecific antibody or variant thereof of the invention, to the individual in need thereof.

The invention further provides an antibody or variant thereof of the invention: preferably a bispecific antibody or variant thereof of the invention, for use in the treatment of an individual that has disease involving aberrant cells such as cancer, or a chronic infection with a virus or parasite.

In a preferred embodiment the parasite is an intracellular parasite.

Further provided is a method of stimulating an immune response in an individual against an aberrant cell in said individual, the method comprising providing (administering to) said individual with an antibody or a variant thereof, preferably a bispecific antibody or a variant thereof of the invention. The aberrant cell is preferably a cancer cell, a virus-infected cell, a parasite or a parasite infected cell. In a preferred embodiment the cell is a cancer cell or a neoplastic cell.

DETAILED DESCRIPTION OF THE INVENTION

T-cell exhaustion is mediated by several inhibitory receptors including programmed cell death protein 1 (PD1). TIM3, and lymphocyte activation gene 3 protein (LAG3). TIM3 is an immune checkpoint inhibitor. It is a protein that can be present on Th1 cells. It is a cell surface protein that regulates macrophage activation and enhances the severity of experimental autoimmune encephalomyelitis in mice. CD4-positive T helper lymphocytes can be divided into several types (including types 1 (Th1) and 2 (Th2)) on the basis of their cytokine secretion patterns. Th1 cells and their associated cytokines are involved in cell-mediated immunity to intracellular pathogens and delayed-type hypersensitivity reactions. TIM-3 or HAVCR2 is known under a number of aliases such as Hepatitis A Virus Cellular Receptor 2: T-Cell Immunoglobulin And Mucin Domain-Containing Protein 3: T-Cell Immunoglobulin Mucin Family Member 3; T-Cell Immunoglobulin Mucin Receptor 3: T-Cell Membrane Protein 3; HAVcr-2: TIMD-3: Tim-3; TIMD3; T Cell Immunoglobulin Mucin 3; T Cell Immunoglobulin Mucin-3; Kidney Injury Molecule-3; CD366; and KIM-3. External Ids for TIM-3 are HGNC: 18437; Entrez Gene: 84868; Ensembl: ENSG00000135077; OMIM: 606652: and UniProtKB: Q8TDQ0.

Galectin-9 or LGALS9 is a known ligand for TIM-3. It is known under a number of different names such as Lectin. Galactoside Binding Soluble 9; Lectin, Galactoside-Binding, Soluble, 9; Tumor Antigen HOM-HD-21; Ecalectin: Gal-9: Urate Transporter/Channel Protein: LGALS9A; and HUAT. External Ids for Galectin-9 are HGNC: 6570: Entrez Gene: 3965; Ensembl: ENSG00000168961: OMIM: 601879: and UniProtKB: O00182.

Programmed Cell Death 1 protein (PD-1) is a cell surface receptor that belongs to the CD28 family of receptors and is expressed on T cells and pro-B cells. PD-1 is presently known to bind two ligands, PD-L1 and PD-L2. PD-1, functioning as an immune checkpoint, plays an important role in down regulating the immune system by inhibiting the activation of T-cells, which in turn reduces autoimmunity and promotes self-tolerance. The inhibitory effect of PD-1 is thought to be accomplished through a dual mechanism of promoting apoptosis (programmed cell death) in antigen specific T-cells in lymph nodes while simultaneously reducing apoptosis in regulatory T cells (suppressor T cells). PD-1 is also known under a number of different aliases such as PDCD1: Programmed Cell Death 1: Systemic Lupus Erythematosus Susceptibility 2: Protein PD-1; HPD-1; PD1: Programmed Cell Death 1 Protein; CD279 Antigen; CD279; HPD-L; HSLE1; SLEB2; and PD-1. External Ids for PD-1 are HGNC: 8760; Entrez Gene: 5133: Ensembl: ENS000000188389; OMIM: 600244; and UniProtKB: Q15116. New classes of drugs that block the activity of PD-1, the PD-1 inhibitors, activate the immune system to attack tumors and are therefore used with success to treat some types of cancer.

PD-L1 is a type 1 transmembrane protein that plays a role in suppressing an immune response during particular events such as pregnancy, tissue allografts, autoimmune disease and other disease states such as hepatitis. The binding of PD-L1 to PD-1 or B7.1 (CD80) transmits an inhibitory signal which reduces the proliferation of the PD-1 expressing T cells. PD-1 is thought to be able to control the accumulation of foreign antigen specific T cells through apoptosis. PD-L1 is expressed by a variety of cancer cells and the expression thereof is thought to be at least in part responsible for a dampening of an immune response against the cancer cell. PD-L1 is a member of the 87-family of protein and is known under a variety of other names such as CD274 Molecule; CD274 Antigen; B7 Homolog 1; PDCD1 Ligand 1: PDCD1LG1; PDCD1L1: B7H1; PDL1; Programmed Cell Death 1 Ligand 1: Programmed Death Ligand 1: B7-H11; and B7-H. External Ids for CD274 are HGNC: 17635; Entrez Gene: 29126; Ensembl: ENSG00000120217; OMIM: 605402; UniProtKB: Q9NZQ7.

PD-L2 is a second ligand for PD-1. Engagement of PD-1 by PD-L2 inhibits T cell receptor (TCR)-mediated proliferation and cytokine production by CD4+ T cells. At low antigen concentrations. PD-L2/PD-1 binding inhibits B7-CD28 signals. At high antigen concentrations. PD-L2/PD-1 binding reduces cytokine production. PD-L expression is up-regulated on antigen-presenting cells by interferon gamma treatment. It is expressed in some normal tissues and a variety of tumors. PD-L1 and PD-L2 are thought to have overlapping functions and regulate T cell responses. The protein is known under a number of other names such as Programmed Cell Death 1 Ligand 2; B7 Dendritic Cell Molecule; Programmed Death Ligand 2: Butyrophilin B7-DC; PDCD1 Ligand 2: PD-1 Ligand 2: PDCD1L2; B7-DC: CD273: B7DC: PDL2; PD-1-Ligand 2; CD273 Antigen: BA574F11.2: and Btdc. External Ids for PD-L2 are HGNC: 18731; Entrez Gene: 80380: Ensembl: ENSG00000197646; OMIM: 605723: and UniProtKB: Q9BQ51.

Reference to sequence identifiers is done to identify which protein is targeted. An antibody of the invention also recognizes at least some variants thereof such as allelic variants, splice variants and mutant variants thereof as long as the epitope recognized by the respective variable domain of the antibody has not been affected. Some of the alternative names may or may not have also been used to refer to other proteins. The names are given for reference purposes only. An antibody of the invention binds to the protein as expressed on cells. It can also bind to variants of the protein as long as the epitope to which the antibody binds is available. Thus splicing variants or mutant proteins (if any) will also be bound as long as the epitope is available. The fact that the antibody binds to the indicated protein means that it can bind to protein as a property and does not imply that the antibody is actually bound to the target, although it can be. It also does not mean that the antibody does not bind to other proteins.

The invention discloses an antibody or variant thereof, which is preferably a bispecific antibody or variant thereof, that binds an extracellular part of a member of the PD-1 (first membrane protein) and an extracellular part of TIM-3 (second membrane protein). Such a (bispecific) antibody is further also referred to as "an antibody or bispecific antibody of the invention". Also provided are compositions and kits of parts comprising two or more (bispecific) antibodies as described herein.

Antibodies typically bind their target via the so-called antigen binding site. An unmodified antigen-binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain comprises a heavy chain variable region (VH) and a light chain variable region (VI). The antigen-binding site can be present in the combined VH/VL variable domain, or in only the VH region or only the VL region. When the antigen-binding site is present in one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity determining regions (CDR) of the antibody and the specific three-dimensional structure of both the antigen and the variable domain allowing these two structures to bind together with precision (an interaction similar to a lock and key), as opposed to random, non-specific sticking of proteins. As an antibody typically recognizes part of an antigen called the epitope of an antigen, and as such epitope may be present in other compounds as well, antibodies according to the present invention may recognize other proteins as well, if such other compounds contain the same epitope. Hence, the term "binding" does not exclude binding of the antibodies to another protein or protein(s) that contain the same epitope. Such other protein(s) is preferably not a human protein.

A protein of the invention such as an antibody typically does not bind to other proteins than the specified target protein on the membrane of cells in a post-natal, preferably adult human.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Preferably, the affinity of the separate arms of the antibodies according to the invention is in the nanomolar range. Antibodies such as the bispecific antibodies of the present invention typically comprise the constant domains (Fc part) of a natural antibody, which may be engineered as described elsewhere herein, for instance, facilitate heterodimerization or to reduce ADCC and/or CDC activity, or other reasons. An antibody of the invention is typically a bispecific full length antibody, preferably of the human IgG subclass.

A variable domain is composed of the variable region of a heavy chain and a variable region of a light chain. The variable region of a heavy chain is typically formed by a rearranged VDJ region. A variable region of a light chain is typically formed by a rearranged VJ region. The VDJ/VJ regions can now also be artificially produced using for instance the large body of sequence information that is available of functional antibodies.

An antibody of the invention is preferably a "full length" antibody. The term 'full length' according to the invention is defined as comprising an essentially complete antibody, without one or more artificially added moieties which a size of larger than 20 amino acid residues, such as for instance additional antigen binding sites or additional activation sites or additional ligands or additional ligand-binding moieties. A full length antibody, however, does not necessarily have all functions of an intact antibody. For the avoidance of doubt, a full length antibody contains two heavy and two light chains. Each chain contains constant (C) and variable (V) regions, which can be broken down into domains designated CH1. CH2, CH3, VH for the heavy chain, and CL, VL for the light chain. The domains of the heavy chains are preferably present in the order of a natural antibody (VH-CH1-CH2-CH3, meaning that the VH domain is adjacent to the CH1 domain, followed by a CH2 domain and subsequently followed by a (CH3 domain). The domains of the light chains are also preferably present in the order of a natural antibody (VL-CL: meaning that the VL domain is adjacent to the CL domain). An antibody binds to antigen via the variable domains contained in the Fab fragment portion. The antibody can interact with molecules and cells of the immune system through the constant domains, mostly through the Fe portion.

In some embodiments, an antibody of the invention is an IgG, preferably a full length IgG. Full length IgG antibodies are preferred because of their typically favorable half-life and the desire to stay as close to fully autologous (human) molecules for reasons of immunogenicity. In some embodiments, an antibody of the invention is a full length IgG1, a full length IgG2, a full length IgG3 or a full length IgG4 antibody.

Full length antibodies according to the invention encompass antibodies wherein mutations may be present that provide desired characteristics or are just alternatives to the ones in the original chain. Such mutations should not be deletions of substantial portions of any of the regions. However, antibodies wherein one or several amino acid residues are acid inserted, deleted, substituted or a combination thereof, without essentially altering the antigen binding characteristics of the resulting antibody are embraced within the term "full length antibody". For instance, an IgC antibody can have 1-20 amino acid residue insertions, substitutions, deletions or a combination thereof in the constant region.

An antibody or a functional part, derivative and/or analogue thereof of the invention is preferably a bispecific antibody or a functional part, derivative and/or analogue thereof. In a preferred embodiment it is a bispecific IgG antibody with reduced effector function. In a preferred embodiment an antibody of the invention is a bispecific full length antibody. An antibody of the invention is preferably a bispecific full length IgG antibody, preferably mutated in the CH2/lower hinge region to reduce effector function. IgG1 which is mutated in the CH2/lower hinge region to reduce effector function is favored based on its long circulatory half-life in man. In order to prevent any immunogenicity in humans it is preferred that the bispecific antibody according to the invention is a human antibody.

The term 'bispecific' (bs) means that one part of the antibody (as defined above) binds to one epitope on an antigen whereas a second part binds to a different epitope on either the same antigen, or a different antigen. The different epitopes are typically present on different antigens. The different epitopes can, however, also be present on the same antigen. According to the present invention, said first and second antigens are in fact two different proteins. A preferred bispecific antibody is an antibody that comprises parts of two different monoclonal antibodies and consequently can bind to two different epitopes, preferably on two different antigens. Dependent on the expression level, (sub-) cellular localization and stoichiometry of the two antigens recognized by a bispecific antibody, both Fab arms of the antibody may or may not simultaneously bind their epitope. One arm of the bispecific antibody typically contains the variable domain of one antibody and the other arm contains the variable domain of another antibody (i.e. one arm of the bispecific antibody is formed by one heavy chain paired with one light chain whereas the other arm is formed by a different heavy chain paired with a light chain). The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same or a common, light chain variable region is also referred to as a bispecific antibody with a common light chain variable region (cLcv). It is preferred that the light chain constant region is also the same. Such bispecific antibodies are referred to as having a common light chain (cLc). Further provided is therefore a bispecific antibody according to the invention, wherein both arms comprise a common light chain.

Bispecific antibodies as described herein preferably comprise a common light chain variable domain, preferably a common light chain. The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain'. 'common LC'. 'cLC'. 'single light chain' with or without the addition of the term 'rearranged' are all used herein interchangeably. The terms 'common light chain variable region'. 'common VL', 'common LCv', 'cLCv', 'single VL' with or without the addition of the term 'rearranged' are all used herein interchangeably. It is a preferred aspect of the present invention that a bispecific antibody has a common light chain (variable region) that can combine with at least two, and preferably a plurality of heavy chains (variable regions) of different binding specificity to form antibodies with functional antigen binding domains WO2009/157771. The common light chain (variable region) is preferably a human light chain (variable region). A common light chain (variable region) preferably has a germline sequence. A preferred germline sequence is a light chain variable region that is frequently used in the human repertoire and has good thermodynamic stability, yield and solubility. A preferred germline light chain is O12. A common light chain is preferably the rearranged germline human kappa light chain $IgV_K1\text{-}39^*01/IGJ_K1^*01$ (FIG. A). The common light chain variable region is preferably the variable region of the rearranged germline human kappa light chain $IgV_K1\text{-}39^*01/IGJ_K1^*01$. A common light chain preferably comprises a light chain variable region as depicted in FIG. 1B, or 1D with 0-5 amino acid insertions, deletions, substitutions, additions or a combination thereof. The common light preferably further comprises a light chain constant region, preferably a kappa light chain constant region. A nucleic acid that encodes the common light chain can be codon optimized for the cell system used to express the common light chain protein. The encoding nucleic acid can deviate from a germ-line nucleic acid sequence.

In a preferred embodiment the light chain comprises a light chain region comprising the amino acid sequence of an $O12/IgV_K1\text{-}39^*01$ gene segment as depicted in FIG. 1A with 0-10, preferably 0-5 amino acid insertions, deletions, substitutions, additions or a combination thereof. The phrase "O12 light chain" will be used throughout the specification as short for "a light chain comprising a light chain variable region comprising the amino acid sequence of an O12/$IgV_K1\text{-}39^*01$ gene segment as depicted in FIG. 1A with 0-10, preferably 0-5 amino acid insertions, deletions, substitutions, additions or a combination thereof. $IgV_K1\text{-}39$ is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for $IgV_K1\text{-}39$ is given in FIG. 1E. This lists the sequence of the V-region. The V-region can be combined with one of five J-regions. FIGS. 1B and 1D describe two preferred sequences for $IgV_K1\text{-}39$ in combination with a J-region. The joined sequences are indicated as IGKV1-39/jk1 and IGKV1-39/jk5: alternative names are $IgV_K1.39^*01/IGJ_K1^*01$ or $IgV_K1\text{-}39^*01/IGJ_K5^*01$ (nomenclature according to the IMGT database worldwide web at imgt.org).

It is preferred that the $O12/IgV_K1\text{-}39^*01$ comprising light chain variable region is a germline sequence. It is further preferred that the $IGJ_K1^*01$ or/$IGJ_K5^*01$ comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline $O12/IgV_K1\text{-}39^*01$. In a preferred embodiment the light chain variable region comprises the kappa light chain $IgV_K1\text{-}39^*01/IGJ_K1^*01$ or $IgV_K1\text{-}39^*01/IGJ_K5^*01$. In a preferred embodiment a $IgV_K1\text{-}39^*01/IGJ_K1^*01$. The light chain variable region preferably comprises a germline kappa light chain $IgV_K1\text{-}39^*01/IGJ_K1^*01$ or germline kappa light chain $IgV_K1\text{-}39^*01/IGJ_K5^*01$, preferably a germline $IgV_K1\text{-}39^*01/IGJ_K1^*01$.

Mature B-cells that produce an antibody with an O12 light chain often produce a light chain that has undergone one or more mutations with respect to the germline sequence. i.e. the normal sequence in non-lymphoid cells of the organism. The process that is responsible for these mutations is often referred to as somatic (hyper)mutation. The resulting light chain is referred to as an affinity matured light chain. Such light chains, when derived from an O12 germline sequence are O12-derived light chains. In this specification, the phrase "O12 light chains" will include O12-derived light chains. The mutations that are introduced by somatic hypermutation can of course also be introduced artificially in the lab. In the lab also other mutations can be introduced without affecting the properties of the light chain in kind, not necessarily in amount. A light chain is at least an O12 light chain if it comprises a sequence as depicted in FIG. 1A, FIG. 1B; FIG. 1D or FIG. 1E with 0-10, preferably 0-5 amino acid insertions, deletions, substitutions, additions or a combination thereof. In a preferred embodiment the O12 light chain is a light chain comprising a sequence as depicted in FIG. 1A; 1B; 1D or 1E with 0-9, 0-8, 0-7, 0-6, 0-5, 0-4 amino acid insertions, deletions, substitutions, additions or a combination thereof. In a preferred embodiment the O12 light chain is a light chain comprising a sequence as depicted in FIG. 1A, FIG. 1B; FIG. 1D or FIG. 1E with 0-5, preferably 0-4, more preferably 0-3 amino acid insertions, deletions, substitutions, additions or a combination thereof. In a preferred embodiment the O12 light chain is a light chain comprising a sequence as depicted in FIG. 1A, FIG. 1B: FIG. 1D or FIG. 1E with 0-2, more preferably 0-1, most preferably 0 amino acid insertions, deletions, substitutions, additions or a combination thereof. In a preferred embodiment the O12 light chain is a light chain comprising a sequence as depicted in FIG. 1A or FIG. 11B with the mentioned amino acid insertions, deletions, substitutions, additions or a combination thereof. In a preferred embodiment the light chain comprises the sequence of FIG. 1A. In a preferred embodiment the light chain variable region comprises the sequence of FIG. 1B.

The common light chain (variable region) can be a lambda light chain and this is therefore also provided in the context of the invention, however a kappa light chain is preferred. The constant part of a common light chain of the invention can be a constant region of a kappa or a lambda light chain. It is preferably a constant region of a kappa light chain, preferably wherein said common light chain is a germline light chain, preferably a rearranged germline human kappa light chain comprising the IgVK1-39 gene segment, most preferably the rearranged germline human kappa light chain IgVK1-39*01/IGJK1*01 (FIG. 1). The terms rearranged germline human kappa light chain $IgV_K1\text{-}39^*01/IGJ_K1^*01$, IGKV1-39/IGKJ1, $huV_K1\text{-}39$ light chain or in short $huV_K1\text{-}39$, or simply 1-39 are used interchangeably throughout the application. Those of skill in the art will recognize that "common" also refers to functional equivalents of the light chain of which the amino acid sequence is not identical. Many variants of said light chain exist wherein mutations (deletions, substitutions, additions) are present that do not influence the formation of functional binding regions.

$IgV_K1\text{-}39$ is short for Immunoglobulin Variable Kappa 1-39 Gene. The gene is also known as Immunoglobulin Kappa Variable 1-39; IGKV139; IKVI-39; O12a or O12. External Ids for the gene are HGNC: 5740; Entrez Gene: 28930: Ensembl: ENSG00000242371. A preferred amino acid sequence for $IgV_K1\text{-}39$ is given in FIG. 1. This lists the sequence of the V-region. The V-region can be combined with one of five J-regions. FIG. 1 describes two preferred sequences for IgV$_K$1-39 in combination with a J-region. The joined sequences are indicated as IGKV1-39/jk1 and IGKV1-39/jk5; alternative names are IgV$_K$1-39*01/ IGJ$_K$1*01 or IgV$_K$1-39*01/IGJ$_K$5*01 (nomenclature according to the IMGT database worldwide web at imgt.org).

A common light chain variable region is preferably linked to a kappa light chain constant region. In a preferred embodiment the light chain comprises the kappa light chain IgV$_K$1-39*01/IGJ$_K$1*01 or IgV$_K$1-9*01/IGJ$_K$5*01. In a preferred embodiment a IgV$_K$1-39*01/IGJ$_K$1*01.

A cell that produces a common light chain can produce for instance rearranged germline human kappa light chain IgV$_K$1-39*01/IGJ$_K$1*01 and a light chain comprising the variable region of the mentioned light chain fused to a lambda constant region.

Bispecific antibodies or variants thereof as described herein preferably have one heavy chain variable region/light chain variable region (VH/VL) combination that binds an extracellular part of PD-1 and a second VH/VL combination that binds an extracellular part of TIM-3. In a preferred embodiment the VL in said first VI/VL combination is similar to the VL in said second VH/VL combination. In a more preferred embodiment, the VLs in the first and second VH/VL combinations are identical. In a preferred embodiment, the bispecific antibody is a full length antibody which has one heavy/light (H/L) chain combination that binds an extracellular part of PD-1 and one H/L chain combination that binds an extracellular part of TIM-3. In a preferred embodiment the light chain in said first H/L chain combination is similar to the light chain in said second II/L chain combination. In a more preferred embodiment, the light chains in the first and second H/L chain combinations are identical.

Several methods have been published to favor the production of the bispecific antibody or vice versa, the monospecific antibodies. In the present invention it is preferred that the cell favors the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of the invention comprises two different immunoglobulin heavy chains with compatible heterodimerization domains. Various compatible heterodimerization domains have been described in the art. The compatible heterodimerization domains are preferably compatible immunoglobulin heavy chain CH3 heterodimerization domains. When wildtype CH3 domains are used, co-expression of two different heavy chains (A and B) and a common light chain will result in three different antibody species, AA, AB and BB. AA and BB are designations for the two mono-specific, bivalent antibodies, and AB is a designation for the bispecific antibody. To increase the percentage of the desired bispecific product (AB) (CH3 engineering can be employed, or in other words, one can use heavy chains with compatible hetero-dimerization domains, as defined hereunder. The art describes various ways in which such hetero-dimerization of heavy chains can be achieved. One way is to generate 'knob into hole' bispecific antibodies. See US Patent Application 20030078385 (Arathoon et al.)

The term 'compatible hetero-dimerization domains' as used herein refers to protein domains that are engineered such that engineered domain A' will preferentially form heterodimers with engineered domain B' and vice versa, homodimerization between A-A' and B'-B' is diminished.

In U.S. Ser. No. 13/866,747 (now issued as U.S. Pat. No. 9,248,181), U.S. Ser. No. 14/081,848 (now issued as U.S. Pat. No. 9,358,286) and PCT/NL2013/050294 (published as WO2013/157954): incorporated herein by reference) methods and means are disclosed for producing bispecific antibodies using compatible heterodimerization domains. These means and methods can also be favorably employed in the present invention. Specifically, a bispecific antibody of the invention preferably comprises mutations to produce essentially only bispecific full length IgG molecules. Preferred mutations are the amino acid substitutions L351K and T366K (EU numbering) in the first CH3 domain (the 'KK-variant' heavy chain) and the amino acid substitutions L351D and L368E in the second domain (the 'DE-variant' heavy chain), or vice versa. It was previously demonstrated in our U.S. Pat. Nos. 9,248,181 and 9,358,286 patents as well as the WO2013/157954 PCT application that the DE-variant and KK-variant preferentially pair to form heterodimers (so-called 'DEKK' bispecific molecules). Homodimerization of DE-variant heavy chains (DEDE homodimers) hardly occurs due to repulsion between the charged residues in the CH3-CH3 interface between identical heavy chains.

Bispecific antibodies can be generated by (transient) transfection of a plasmid encoding a light chain and two different heavy chains that are CH3 engineered to ensure efficient hetero-dimerization and formation of the bispecific antibodies. The production of these chains in a single cell leads to the favored formation of bispecific antibodies over the formation of monospecific antibodies. Preferred mutations to produce essentially only bispecific full length IgG1 molecules are amino acid substitutions at positions 351 and 366. e.g. L351K and T366K (numbering according to EU numbering) in the first CH3 domain (the 'KK-variant' heavy chain) and amino acid substitutions at positions 351 and 368. e.g. L351D and L368E in the second CH3 domain (the 'DE-variant' heavy chain), or vice versa.

The Fe region mediates effector functions of an antibody, such as complement-dependent cytotoxicity (CDC), antibody-dependent cellular cytotoxicity (ADCC) and antibody-dependent cell phagocytosis (ADCP). Depending on the therapeutic antibody or Fe fusion protein application, it may be desired to either reduce or increase the effector function. Reduced effector functions are preferred in the present invention. Reduced effector function can be desired when an immune response is to be activated, enhanced or stimulated as in some of the embodiments of the invention. Antibodies with reduced effector functions can be used to target cell-surface molecules of immune cells, among others.

Binding of IgG to the FcγRs or C1q was found to require residues located in the hinge region and the CH2 domain. Two regions of the CH2 domain (FIG. 2D) are relevant for FcγRs and C1q binding. Substitutions into human IgG1 of IgG2 residues at positions 233-236 and IgG4 residues at positions 327, 330 and 331 were shown to greatly reduce ADCC and CDC (Armour et al., 1999. Eur J Immunol. 29(8):2613-24; Shields et al., 2(00. J Biol Chem. 276(9): 6591-604). Furthermore, Idusogie et al. demonstrated that alanine substitution at different positions, including K322, significantly reduced complement activation (Idusogie et al., 2000. J Immunol. 164(8):4178-84.

Due to their reduced effector functions, IgG4 antibodies represent an IgG subclass for receptor blocking without cell depletion. IgG4 molecules can exchange half-molecules in a dynamic process termed Fab-arm exchange. This phenomenon can occur between therapeutic antibodies and endogenous IgG4. The S228P mutation is an example of a mutation that ensures reduced capacity to Fab-arm exchange. (Labrijn, et al., 2009. Nat Biotechnol. 27(8):767-71.

Antibodies with reduced effector functions are preferably IgG antibodies comprising a modified CH2/lower hinge region, for instance to reduce Fc-receptor interaction or to reduce C1q binding. In some embodiments the antibody of the invention is an IgG antibody with a mutant CH2 and/or lower hinge domain such that interaction of the bispecific IgG antibody to a Fc-gamma receptor is reduced. An antibody comprising a mutant CH2 region is preferably an IgG1 antibody. Such a mutant IgG1 CH2 and/or lower hinge domain preferably comprise an amino substitution at position 235 and/or 236 (numbering according to EU numbering), preferably an L235G and/or G236R substitution (FIG. 2E).

A variant of an antibody or bispecific antibody as described herein comprises a functional part, derivative and/or analogue of the antibody or bispecific antibody. The variant maintains the binding specificity of the (bispecific) antibody. The functional part, derivative and/or analogue maintains the binding specificity of the (bispecific) antibody. Binding specificity is defined by capacity to bind an extracellular part of PD-1 and TIM-3 as described herein.

A functional part of an antibody, or preferably a functional part of a bispecific antibody as described herein is a part comprising a variable domain that binds an extracellular part of PD-1 and a variable domain that an extracellular part of TIM-3. A suitable part is for instance an F(ab')2 fragment as created by digestion of a bispecific antibody with pepsin. Other parts comprising said variable domains are included in the present invention.

A functional derivative of an antibody, or preferably a functional derivative of a bispecific antibody as described herein is a protein comprising a variable domain that binds an extracellular part of PD-1 and a variable domain that binds an extracellular part of TIM-3 that are linked by a linker. The variable domains may be variable domains as such, or Fab fragments or variable domain like molecules such as single chain Fv fragments comprising a VH and a VL linked together via a linker. Other examples of variable domain like molecules are so-called single domain antibody fragment. A single-domain antibody fragment (sdAb) is an antibody fragment with a single monomeric variable antibody region. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable regions, one from a light and one from a heavy chain). Single-domain antibodies by themselves are not much smaller than normal antibodies (being typically 90-100 kDa). Single-domain antibody fragments are mostly engineered from heavy-chain antibodies found in camelids; these are called VHH fragments (Nanobodies®). Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. Other non-limiting examples of variable domain-like molecules are VHH, Human Domain Antibodies (dAbs) and Unibodies. Preferred functional parts are parts that comprise variable domains comprising a heavy chain variable region and a light chain variable region. Non-limiting examples of such variable domains are F(ab)-fragments and Single chain Fv fragments. Bispecific formats for variable domain(-like) linkage are for instance Human Serum Albumine (ISA) bound to two different scFv; bispecific mini-antibodies comprising two different scFv bound together via a dimerization motifs or self-associating secondary structures such as helix bundles or coiled coils to bring about dimerization of the scFv fragments (Morrison (2007) Nat. Biotechnol 25:1233-34). Examples of suitable HSA linkers and method for coupling scFv to the linker are described in WO2009/126920.

An antibody or functional part, derivative and/or analogue thereof or preferably a bispecific antibody or functional part, derivative and/or analogue thereof of the present invention is preferably used in humans. To this end an antibody or functional part, derivative and/or analogue thereof of the invention is preferably a human or humanized antibody. Tolerance of a human to a polypeptide is governed by many different aspects. Immunity, be it T-cell mediated. B-cell mediated or other is one of the variables that are encompassed in tolerance of the human for a polypeptide. The constant region of a bispecific antibody of the present invention preferably comprises a human heavy chain constant region, preferably comprising a sequence as depicted in FIG. 2; and a human light chain constant region, preferably comprising a sequence as depicted in FIG. 1C. The constant region may contain one or more, preferably not more than 10, preferably not more than 5 amino-acid differences with the constant region of a naturally occurring human antibody. It is preferred that the constant part is entirely derived from a naturally occurring human antibody. Such derived sequence may be engineered for specific purposes, for instance to facilitate heterodimerization or to reduce ADCC and/or CDC activity, and other reasons. Various antibodies produced herein are derived from common light chain mice immunized with the respective target as described in WO2009/157771. Various antibodies produced herein are derived from a human antibody variable domain library. As such these variable domains are human. The unique CDR regions may be derived from humans, be synthetic or derived from another organism. The variable region is at least a human variable region when it has, with the exception of the CDR regions, an amino acid sequence that is identical to an amino acid sequence of the variable region of a naturally occurring human antibody. In such embodiments, the VH of a variable domain of an antibody that binds an extracellular part of PD-1 or TIM-3, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3D-structure of the murine heavy chain variable region; de-immunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

De-immunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

An antibody or bispecific antibody or functional part, derivative and/or analogue thereof according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG constant regions. i.e. selected from the group consisting of IgG1, IgG2, IgG3 and IgG4. Preferably said constant region is an IgG4 or IgG1 constant region (FIG. 2), more preferably a mutated IgG1 constant region. Some variation in the constant region of IgG1 occurs in nature and/or is allowed without changing the immunological properties of the resulting antibody. Typically between about 1-10 amino acid insertions, deletions, substitutions or a combination thereof are allowed in the constant region. The constant region may be mutated as indicated herein for enabling efficient heterodimerization, for reducing effector function or for other reasons including half-life, stability and the like.

Rational methods have evolved toward minimizing the content of non-human residues in the human context. Various methods are available to successfully graft the antigen-binding property of an antibody onto another antibody. The binding properties of antibodies may rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagrol and J. Fransson (2(008) Frontiers in Bioscience 13, 1619-1633, which is included by reference herein.

The light chain variable region of a variable domain comprising a variable heavy chain sequence as depicted in FIG. 3, is preferably a germline light chain of or based on O12, preferably the rearranged germline human kappa light chain $IgV_K1-39*01/IGJ_K1*01$ or a fragment or a functional derivative thereof (nomenclature according to the IMGT database worldwide web at imgt.org). The terms rearranged germline human kappa light chain $IgV_K1.39*01/IGJ_K1*01$, IGKV1-39/ICKJ1, $huV_K1-39$ light chain or in short $huV_K1-39$ are used. The light chain can have 1, 2, 3, 4 or 5 amino acid insertions, deletions, substitutions or combination thereof. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain. A preferred sequence for the common light chain is depicted in FIG. 1.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. The two essentially identical light chains can be light chains with essentially the same light chain variable regions and different light chain constant regions or, preferably, two essentially identical light chain constant regions. This concept is in the art also referred to as the "common light chain" method. When the essentially identical light chains work together with the two different heavy chains allowing the formation of variable domains with different antigen-binding sites and concomitant different binding properties, the ratio of bispecific antibody to other antibody that is produced by the cell is significantly improved over the expression of two essentially different light chains. The ratio of bispecific antibody that is produced by the cell can be further improved by stimulating the pairing of two different heavy chains with each other over the pairing of two identical heavy chains. The art describes various ways in which such hetero-dimerization of heavy chains can be achieved. A preferred method is described in U.S. provisional application 61/635,935, which has been followed up by US regular application Ser. No. 13/866,747 and CT application No. PCT/NL2013/050294 (WO 2013/157954 A1), which are incorporated herein by reference. Methods and means are disclosed for producing bispecific antibodies (from a single cell), whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that are capable of forming an interface, said method comprising providing in said cell a) a first nucleic acid molecule encoding a 1st (CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell. The host cell comprises at least one light chain, and preferably a common light chain.

A preferred embodiment provides a method for producing a bispecific antibody according to the invention from a single cell, wherein said bispecific antibody comprises two CH3 domains that are capable of forming an interface, said method comprising providing:

a cell having a) a first nucleic acid molecule encoding a heavy chain comprising an antigen binding site that can bind to an extracellular part of PD-1 and that contains a 1st CH3 domain, and b) a second nucleic acid molecule encoding a heavy chain comprising an antigen-binding site that can bind to an extracellular part of TIM-3 and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on O12, preferably it is the rearranged germline human kappa light chain IgV$_K$1 39*01/ IGJ$_K$1*01, as described above. Means for preferential pairing of said 1st and said 2nd CH3 domain are preferably the corresponding mutations in the CH3 domain of the heavy chain coding regions. The preferred mutations to produce essentially only bispecific antibodies are the amino acid substitutions L351K and T366K (numbering according to EU numbering) in the first (CH3 domain and the amino acid substitutions L351D and L368E in the second CH3 domain, or vice versa (FIG. 2). Further provided is therefore a method according to the invention for producing a bispecific antibody, wherein said first CH3 domain comprises the amino acid substitutions L351K and T366K (numbering according to EU numbering) and wherein said second CH3 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to the invention for producing a bispecific antibody, wherein said first CH-3 domain comprises the amino acid substitutions L351D and L368E (numbering according to EU numbering) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

A variable domain that "blocks" the binding of PD-1 to PD-L1 and/or PD-L2 interferes with binding of PD-1 to PD-L1 and/or PD-L2. Such a variable domain can bind PD-1. Such a blocking variable domain can bind an epitope on PD-1 and compete with PD-L1 and/or PD-L2 for binding to the epitope. Such a blocking variable domain and PD-L1 and/or PD-L2 can also bind to different epitopes on PD-1. In such cases the blocking activity can for instance be due to diminished binding of the PD-L1 and/or PD-L2, displacement of PD-L1 and/or PD-L2 when it is already bound to PD-1 or can prevent binding to PD-1 through steric hindrance. All these and other mechanisms can, at least partially, prevent that said binding partner binds to said first membrane protein.

A variable domain that "blocks" the binding of TIM-3 to Galectin-9 interferes with binding of TIM-3 to Galectin-9. Such a variable domain binds TIM-3. Such a blocking variable domain binds an epitope on TIM-3 and competes with Galectin-9 for binding to the epitope. Such a blocking variable domain and Galectin-9 can also bind to different epitopes on TIM-3. In such cases the blocking activity can be due to diminished binding of the PD-L1 and/or PD-L2, displacement of Galectin-9 when it is already bound to TIM-3 or prevent binding to TIM-3 through steric hindrance. All these and other mechanisms can, at least partially, prevent that said binding partner bind to said first membrane protein.

A variable domain that blocks the binding of a specific binding pair (i.e. PD-1/PD-L1: PD-1/PD-L2 or TIM-3/Galectin-9) as described herein typically reduces binding of the pair when compared to the binding in the absence of the variable domain. This is preferably measured in an in vitro assay. Typically this is done by incubating the variable domain with the membrane protein that it can bind to and subsequently incubating the mixture with the other member of the pair. The binding of the pair is then compared with the binding of the pair in the absence of the variable domain. A variable domain can completely prevent the binding of the first membrane protein to a binding partner thereof. It can also partially prevent the binding of the binding pair. A variable domain that blocks the binding of a specific binding pair of membrane proteins preferably reduces binding of the pair by at least 50%, preferably at least 60%, preferably at least 70%, preferably at least 80%, and more preferably at least 90% when compared to the binding in the absence of the variable domain. Blocking of binding by a variable domain is defined herein as the blocking obtained using a bivalent monoclonal antibody comprising said two of the same of said variable domains. The variable domain of course also blocks the binding when present in an antibody comprising said variable domain and a variable domain that binds a second membrane protein.

Specific variable domains that can bind an extracellular part of PD-1 and that at least partially block the binding of PD-1 to PD-L1 and/or PD-L2 are variable domains that comprise the amino acid sequence of the VH of: MF6076: MF6226; MF6236: MF6256; MF6930; MF6932: MF6935; MF6936; MF6972: MF6974: and MF6982. Specific variable domains that can bind an extracellular domain of TIM-3 and that block the binding of TIM-3 to Galectin-9 are variable domains that comprise the amino acid sequence of the VII of MF7676; MF7677: MF7678; MF7679. The amino acid sequences are depicted in FIG. 3.

The invention also provides a method of engaging and/or activating T-cells comprising providing a system comprising a T-cell and a cell (second cell) to which said T-cell is to be engaged or activated, and providing said system with at least one antibody, preferably at least one bispecific antibody, that comprises a variable domain that can bind PD-1 and a variable domain that can bind TIM-3 and incubating said system under conditions that are permissive for the T-cell to become engaged and/or activated. In some embodiments, said method is an in vitro method. The cell to which said T-cell is to be engaged or activated is preferably an immune cell, for example an antigen presenting cell, a macrophage, a neoplastic cell, a virus infected cell, or an intracellular parasite infected cell. Engaging and/or activating T-cells directs T-cells to a specific target. Activating a T-cell is activating the T-cell receptor of said T-cell. Engaging a T-cell typically is activating a T-cell. Engagement can also direct an already activated T-cell to a target specified by the antibody. Conditions that are permissive for said T-cell to become engaged and/or activated are typically culture conditions but can also be incubation in a non-humananimal. The conditions are such that the T-cell is not engaged in the absence of the antibody. If collections of T-cells are measured some of these can be already engaged or activated provided that the collection contains sufficient T-cells that are not engaged or activated.

An antibody of the invention can bring two cells together in close proximity that allows the interactions between the cells mediated by proteins other than the PD-1 and TIM-3 bound by the antibody of the invention. One such interaction is an interaction of a T-cell receptor of one cell and MIC on the other cell.

In one aspect the invention provides a method for interfering with PD-1 and/or TIM-3 mediated inhibition in a PD-1 and/or TIM-3 positive cell, the method comprising contacting said cell with an antibody or a functional part, derivative and/or analogue thereof that comprises
    a variable domain that can bind to an extracellular part of PD-1 and
    a variable domain thereof that can bind to an extracellular part of TIM-3, thereby inhibiting PD-1 and/or TIM-3 mediated activity in said cell.

A TIM-3 or PD-1 positive cell expresses the membrane protein on the cell membrane in amounts that can be detected, typically by means of immune fluorescence with a monoclonal antibody specific for the membrane protein. The PD-1 positive cell is a T-cell. The TIM-3 cell is preferably a T-cell, more preferably a so-called exhausted T-cell. T cell exhaustion is a state of T cell dysfunction that arises during many chronic infections and cancer. It is defined by poor effector function, sustained expression of inhibitory receptors and a transcriptional state distinct from that of functional effector or memory T cells. Exhaustion prevents optimal control of infection and tumors. An antibody of the invention interferes with PD-1 and TIM-3 mediated inhibition by binding to the respective membrane proteins and preventing stimulation of the proteins by the respective binding partners of the protein. Known binding partners for PD-1 are PD-L1 and PD-L2. A known binding partner of TIM-3 is Galectin-9. The antibody blocks the interaction of PD-1 with PD-L1 and/or PD-L2: and/or TIM-3 and Galectin-9 and thereby at least in part prevents the inhibitory activity of the PD-1 in the PD-1 positive cell: and/or the inhibitory activity of TIM-3 in a TIM-3 positive cell. In a preferred embodiment of the invention the binding of said PD-1 binding variable domain to PD-1 blocks the binding of PD-1 to PD-L1 and/or PD-L2, preferably PD-L1. In a preferred embodiment of the invention the binding of said TIM-3 binding variable domain to TIM-3 blocks the binding of TIM-3 to Galectin-9. Inhibition of the PD-1 and/or TIM-3 mediated activity in said cell can be measured in various ways. Typically, though not necessarily, the activity is measured by measuring activation of CD4' or CD8' T cells. This can be done by using healthy CD4+ or CD8+ T cells, but an effect on exhaustion is typically best measured on exhausted T-cells. Such T-cells are, for instance, positive for TIM-3. Activity is preferably measured in HTV-specific T-cells, preferably collected from subjects with progressive disease.

Proliferation is a suitable parameter. Proliferation rates can be determined in the presence and the absence of the antibody. Differences in proliferation rates are a measure for the level of inhibition of the activity of TIM-3 and or PD-1 in these cells. Other examples of suitable T-cells are TIL collected from subjects with non-small-cell lung carcinoma (NSCLC). Interferon-gamma production is a suitable parameter. Interferon-gamma production can be determined in the presence and the absence of the antibody. Differences in Interferon-gamma production are a measure for the level of inhibition of the activity of TIM-3 and or PD-1 in these cells. An increase in the proliferation and/or interferon-gamma production is indicative for inhibition of the activity of TIM-3 and or PD-1 in these cells. In a preferred embodiment the increase is an increase of at least 10%, preferably at least 20% more preferably at least 40% more preferably at least 80% over the level or rate detected in the absence of the antibody.

The invention further provides a method for stimulating the formation, stability and/or activity of an immunological synapse comprising providing a system that comprises at least two cells capable of associating with each other via an immunological synapse and providing said system with an antibody or a functional part, derivative and/or analogue thereof that comprises
    a variable domain that can bind to an extracellular part of PD-1 and
    a variable domain that can bind to an extracellular part of TIM-3.
    thereby stimulating the formation, stability and/or activity of an immunological synapse between said at least two cells. The antibody facilitates the formation, stability and/or activity of an immunological synapse by binding to PD-1 and/or TIM-3 on a cell that contains the PD-1 or TIM-3 on the cell membrane. The binding inhibits the activity of PD-1 and/or TIM-3. This has the effect that the formation, stability and/or activity of an immunological synapse is stimulated. The variable domain that can bind PD-1 preferably blocks the binding of PD-1 to PD-L1 and/or PD-L2, preferably PD-L1. The variable domain that can bind TIM-3 preferably blocks the binding of TIM-3 to Galectin-9. Said two cells are cells that are capable of forming an immunological synapse. At least one of the cells is a T-cell receptor positive cell. The other cell is typically, though not necessarily an antigen presenting cell. An immunological synapse forms as a result of the tight apposition of a T cell with an antigen-presenting cell (APC) and it is the site where the T-cell receptor (TCR) is triggered by its antigen ligand, the peptide-MHC complex present in the APC membrane. The immunological synapse in the T-cell membrane typically has three concentric rings of membrane receptors and their underlying cytoskeletal and signaling proteins. The inner circle, or central supramolecular activation cluster (cSMAC), concentrates most of the TCR and CD28, and it is surrounded by the peripheral SMAC that is formed by integrins. Finally, the most external ring or distal SMAC (dSMAC) is where proteins with large ectodomains are located, such as CD43 and CD45, far from the cSMAC.

The invention further provides an antibody or variant thereof that comprises a variable domain that can bind to an extracellular part of PD-1 and a variable domain that can bind to an extracellular part of TIM-3.

In a preferred embodiment of a method, antibody (or variant thereof) or use of the invention the variable domain that binds PD-1 preferably blocks the binding of PD-1 to PD-L1 and/or PD-L2. The variable domain that binds TIM-3 preferably blocks the binding of TIM-3 to Galectin-9. Preferably both variable domains block the binding of the respective binding partners.

The variable domain that binds an extracellular part of PD-1 is preferably defined as a variable domain that when in a bivalent monospecific antibody format that comprises one of said variable domains that bind PD-1, inhibits PD-1/PD-L1 mediated inhibition of T cell receptor mediated activation of a Jurkat cell in a range of 20-150% when compared to the inhibition obtained with the antibody Nivolumab on a Jurkat cell.

The inhibition of PD-1 inhibition of TCR mediated activation of the Jurkat cell is preferably in the range of 50-150%, preferably 80-150%, more preferably 100-150% when compared to the inhibition obtained with the antibody Nivolumab on said Jurkat cell. In a preferred embodiment the inhibition is at least 100% when compared to the inhibition obtained with the antibody Nivolumab on said Jurkat cell. PD-1 inhibition of TCR mediated activation of Jurkat cells is preferably measured by measuring an immune dampening effect of PD-1/PD-L1 binding in Jurkat cells that are incubated under conditions that would, but for the presence of the antibody or functional part, derivative and/or analogue thereof, be activated via the T-cell receptor.

The invention further provides a composition or kit of parts comprising two or more antibodies or functional parts, derivatives and/or analogues thereof, that comprise a variable domain that can bind to an extracellular part of PD-1 and a variable domain that can bind to an extracellular part of a TIM-3;
  wherein a first and a second of said antibodies or functional parts, derivatives and/or analogues thereof bind
    different epitopes on PD-1;
    different epitopes on TIM-3; or
    different epitopes on PD-1 and TIM-3. Embodiments comprising a method, a use, a composition or kit of parts involving two or more antibodies or functional parts, derivatives and/or analogues thereof that have variable domains that bind PD-1 and TIM-3 as specified in this paragraph are also referred to as "Oligoclonics" embodiments. Examples of such Oligoclonics embodiments are embodiments with said first and second antibody. 'Oligoclonics' is a registered trademark. General methods for making such Oligoclonics® products are disclosed in WO 2013/157953 and WO2004/009618 and are incorporated here by reference.

In Oligoclonics embodiments the first and second antibody comprise variable domains that bind PD-1 and TIM-3. Antibodies that have variable domains that bind the same PD-1 or TIM-3 can bind the same individual protein, but this is not necessarily so. An antibody of the invention that binds to PD-1 or TIM-3 binds an epitope on said protein. An epitope is the part of an antigen, in this case the membrane protein that is recognized by the antibody. First and second antibodies that bind different epitopes on a membrane protein can bind the same individual protein on the membrane. To this end the different epitopes are preferably non-overlapping epitopes. In other words the different epitopes are sufficiently separated on the membrane protein that two antibodies can bind simultaneously to the same individual protein. It was surprisingly found that Oligoclonics (a combination of a first and second or more antibodies) can be more effective than the same amount of each of the antibodies alone.

Preferably at least one of the two or more antibodies or functional parts, derivatives and/or analogues comprises a PD-1 binding variable domain that blocks the binding of PD-1 to PD-L1 and/or PD-L2, preferably PD-L1. In a preferred embodiment at least two of the two or more antibodies or functional parts, derivatives and/or analogues comprise a PD-1 binding variable domain that blocks the binding of PD-1 to PD-L1 and/or PD-L2, preferably PD-L1.

Preferably at least one of the two or more antibodies or functional parts, derivatives and/or analogues comprises a TIM-3 binding variable domain that blocks the binding of TIM-3 to Galectin-9. In a preferred embodiment at least two of the two or more antibodies or functional parts, derivatives and/or analogues comprise a TIM-3 binding variable domain that blocks the binding of TIM-3 to Galectin-9.

Preferably at least one of the two or more antibodies or functional parts, derivatives and/or analogues comprises a PD-1 binding variable domain that blocks the binding of PD-1 to PD-L1 and/or PD-L2, preferably PD-L1 and a TIM-3 binding variable domain that blocks the binding of TIM-3 to Galectin-9. Preferably at least two of the two or more antibodies or functional parts, derivatives and/or analogues comprise a PD-1 binding variable domain that blocks the binding of PD-1 to PD-L1 and/or PD-L2, preferably PD-L1 and a TIM-3 binding variable domain that blocks the binding of TIM-3 to Galectin-9.

In one aspect the invention provides methods and uses as described herein wherein two or more antibodies or functional parts, derivatives and/or analogues thereof are used and wherein the two or more antibodies or functional parts, derivatives and/or analogues thereof comprise a variable domain that can bind to an extracellular part of PD-1 and a variable domain that can bind to an extracellular part of a TIM-3:
  wherein a first and a second of said antibodies or functional parts, derivatives and/or analogues thereof bind
    different epitopes on PD-1;
    different epitopes on TIM-3: or
    different epitopes on PD-1 and TIM-3. The preference for blocking binding of PD-L1 and/or PD-L1 by the variable domains that bind PD-1; and the blocking of binding of TIM-3 to Galectin-9 by the variable domains that bind TIM-3 are the same as a described in the Oligoclonics embodiments.

An antibody or a part, derivative, or analogue thereof, preferably comprises two variable domains as described. Such an antibody is preferably a bispecific antibody or a functional part derivative or analogue thereof. Two or more antibodies or functional parts, derivatives and/or analogues thereof can be linked together. Various methods are known in the art. A suitable method is conjugation. In addition, the technology of making multi-specific antibodies has progressed to also include bispecific antibodies that have the same overall structure as a normal mono-specific antibody but wherein the two arms of the antibody each bind a different target. The bispecific antibody or functional part, derivative and/or analogue thereof preferably has two heavy chains with compatible heterodimerization domains. The light chain is preferably a common light chain. The antibody is preferably a full length bispecific antibody that consists of two heavy chains with compatible heterodimerization domains. The light chain is preferably a common light chain.

As used herein, the term "conjugate" refers to two or more molecules that have been covalently joined, optionally by a linking region. For example, in some embodiments, a conjugate is a first protein or non-protein moiety joined to a second protein or non-protein moiety by a linking region. For example, in some embodiments of a binding molecule of the invention it comprises or consists of two or more antibodies that have been covalently joined. A conjugate is not limited to a first and second moiety but in some embodiments may also have a third, fourth or more moieties joined by further linking regions. Examples of protein moieties include, but are not limited to: a polypeptide, a peptidomimetic or an antibody (or antibody part, derivative, or analogue, as described elsewhere in the application). Examples of non-protein moieties include, but are not limited to aptamers. Numerous types of linker can be used, and the linker will be selected to be appropriate according to the molecule types in the conjugate and on the desired properties of the linker (length, flexibility, resistance to protease activity and other similar characteristics). Such linkers may comprise nucleotides, polypeptides, or a suitable synthetic material. For example, a linker may be a flexible peptide linker. In certain embodiments, the linker may be a cleavable linker, allowing the parts of the conjugate to be separated from each other. In other embodiments, a peptide linker might be a helical linker. Various examples and kits for linking proteins and other molecules are well known in the art. As used herein, the term "fusion protein" refers to a protein that comprises two or more polypeptides or proteins that have been joined at the DNA level by recombination and are expressed together as a single polypeptide. A fusion protein may also comprise a peptide linking region also encoded by the DNA and expressed together with the fusion protein. A peptide linker that is part of a fusion protein may be designed to have particular characteristics such as flexibility, hydrophilicity, protease-resistance, cleavability etc. All these properties can be designed within the DNA sequence and methods for designing linkers are well known in the art. For example, antibodies can be linked together by methods well-known in the art, and as described herein, to form bispecific or multi-targeting antibodies. Furthermore, bispecific antibodies can be constructed by various methods known in the art, for example, by using technology such as Biclonics® (see for instance WO2013/157954). A bispecific monoclonal antibody (BsMAb, BsAb) typically comprises binding domains of two different monoclonal antibodies and consequently binds to two different epitopes. Biclonics® molecules, but also other full length IgG bispecific antibodies have two different antigen binding specificities encoded by two different variable regions of a full length IgG molecule of a Fab of a scFv. Biclonics® can be produced by co-transfection of individual cells with genetic constructs encoding two different common light chain (cLC) antibodies as detailed elsewhere herein. CH3 engineering ensures efficient hetero-dimerization and formation of essentially pure bispecific antibodies.

An antibody of the present invention is preferably a bispecific antibody. Antibodies typically bind their target via the so-called antigen binding site. An unmodified antigen-binding site is typically formed by and present in a variable domain of the antibody. A variable domain contains the antigen-binding site. A variable domain that can bind an antigen is a variable domain comprising an antigen-binding site that can bind to an antigen.

An antibody variable domain typically comprises a heavy chain variable region (VH) and a light chain variable region (VL). The antigen-binding site can be present in the combined VH/VL variable domain, or in only the VII region or only the VL region. When the antigen-binding site is present in one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity determining regions (CDR) of the antibody and the specific three-dimensional structure of both the antigen and the variable domain allowing these two structures to bind together with precision (an interaction similar to a lock and key), as opposed to random, non-specific sticking of proteins. As an antibody typically recognizes part of an antigen called the epitope of an antigen, and as such epitope may be present in other compounds as well, antibodies according to the present invention may recognize other proteins as well, if such other compounds contain the same epitope. Hence, the term "binding" does not exclude binding of the antibodies to another protein or protein(s) that contain the same epitope. Such other protein(s) is preferably not a human protein.

An antibody typically does not bind to other proteins than the specified target protein on the membrane of cells in a post-natal, preferably adult human.

A variable domain in an antibody or a functional part, derivative and/or analogue thereof of the invention that can bind an extracellular part of PD-1 binds to PD-1 and, under otherwise identical conditions, at least 100-fold lower to the extracellular part of another member of the CD28 family of the same species. A variable domain of an antibody or a functional part, derivative and/or analogue thereof that binds PD-1 binds to PD-1 and, under otherwise identical conditions, at least a 100-fold lower to the CD28, CTLA4, ICOS. BTLA. NKp30 and TMIGD2 of the same species. Considering that PD-1 is a cell surface protein, the binding is typically assessed on cells that express a member on a cell surface.

A variable domain in an antibody or a functional part, derivative and/or analogue thereof of the invention that can bind an extracellular part of TIM-3 binds to TIM-3 and, under otherwise identical conditions, at least 100-fold lower to the extracellular part of another member of the TIM family of the same species. A variable domain of an antibody or a functional part, derivative and/or analogue thereof that binds TIM-3 binds to TIM-3 and, under otherwise identical conditions, at least a 100-fold lower to TIM-1 or TIM-4 of the same species. Considering that TIM-3 is a cell surface protein, the binding is typically assessed on cells that express a member on a cell surface.

The invention also provides a method for the treatment of an individual that has a cancer, the method comprising administering an antibody or a functional part, derivative and/or analogue of the invention or a bispecific antibody of the invention to the individual in need thereof. The individual is preferably an individual that has a cancer. In some embodiments, the cancer is a cancer that comprises cancer cells that express a membrane protein. In a preferred embodiment the cancer is a cancer that comprises cancer cells that express PD-L1, PD-L2 and or Galectin-9.

The cancer is preferably an adenocarcinoma. Preferred cancers are colorectal cancer; pancreatic cancer; lung cancer: breast cancer; liver cancer; prostate cancer; ovarian cancer; cervical cancer; endometrial cancer; head and neck cancer; melanoma; testis cancer: urothelial cancer: renal cancer; stomach cancer; or carcinoid cancer. In a preferred embodiment the cancer is colorectal cancer; pancreatic cancer; lung cancer; breast cancer: liver cancer: prostate cancer; ovarian cancer; cervical cancer; endometrial cancer; head and neck cancer: or melanoma. In a particularly preferred embodiment the cancer is colorectal cancer; pancreatic cancer; lung cancer: breast cancer; or liver cancer. In a particularly preferred embodiment the cancer is a gastrointestinal cancer. In a preferred embodiment the cancer is colorectal cancer. In this embodiment the antibody or functional part, derivative and/or analogue thereof is preferably an antibody with a variable domain that can bind PD-1 and a variable domain that can bind TIM-3. A PD-1 binding variable domain preferably blocks the binding of PD-1 to PD-L1 and/or PD-L2, preferably PD-L1. A TIM-3 binding variable domain preferably blocks the binding of TIM-3 to Galectin-9. Preferably the method comprises two or more of said antibodies or functional parts thereof, as described for an Oligoclonics embodiment.

Further provided is a method for stimulating an immune response in an individual against an aberrant cell in said individual, the method comprising providing said individual with an antibody or a functional part, derivative and/or analogue thereof of the invention. The aberrant cell is preferably a cancer cell, a virus-infected cell, a parasite or a parasite infected cell. In a preferred embodiment the cell is a cancer cell or a neoplastic cell. In this embodiment the antibody or functional part, derivative and/or analogue thereof is preferably an antibody with a variable domain that can bind PD-1 and a variable domain that can bind TIM-3. In this embodiment a PD-1 binding variable domain preferably blocks the binding of PD-1 to PD-L1 and/or PD-L2, preferably PD-L1. A TIM-3 binding variable domain preferably blocks the binding of TIM-3 to Galectin-9. Preferably the method comprises two or more of said antibodies or functional parts thereof, as described for an Oligoclonics embodiment.

A neoplasm is an abnormal growth of tissue and when it also forms a mass is commonly referred to as a tumor. A neoplasm in the present invention typically forms a mass. A neoplastic cell is a cell from a neoplasm that has formed a mass. The World Health Organization (WHO) classifies neoplasms into four main groups: benign neoplasms, in situ neoplasms, malignant neoplasms, and neoplasms of uncertain or unknown behavior. Malignant neoplasms are also simply known as cancers.

Stimulating an immune response encompasses inducing an immune response and enhancing an already existing immune response. The immune response in an individual can be measured by measuring where applicable: the tumor load of the individual: the virus load of the individual: the parasite load of the individual.

Said virus-infected cell is preferably a cell infected with an immune-deficiency virus, a herpes virus, preferably a herpes simplex virus, a varicella-zostervirus, a cytomegalovirus or an Epstein-Barr virus, a papilloma virus, a hepatis virus, preferably a hepatitis A. B or C virus, a measles virus or an adenoviruses. The virus is preferably a virus known to be able to persist in an individual. Persistent infections are characterized as those in which the virus is not cleared but remains in specific cells of infected individuals. Persistent infections may involve stages of both silent and productive infection without rapidly killing or even producing excessive damage of the host cells. Persistent virus-host interaction may be a latent, a chronic and/or a slow infection.

A parasite-infected cell is a cell that is infected with an intracellular parasite. Such parasites are parasitic microorganisms that are capable of growing and reproducing inside the cells of a host. Some intracellular parasites can also live outside a cell. Such parasites are so-called facultative intracellular parasites. Non-limiting examples are *Listeria monocytogenes, Legionella*, certain species of *mycobacterium* and *Cryptococcus neoformans*. Preferred intracellular parasites are parasites that cannot grow outside host cells, preferred examples are *Chlamydia*, and closely related species, certain species of *mycobacterium* such as *Mycobacterium leprae*, certain protozoa, including: Apicomplexans (*Plasmodium* spp., *Toxoplasma gondii* and *Cryptosporidium parvum* and trypanosomatids.

The invention also provides a nucleic acid molecule that encodes an antibody heavy chain variable region according to the invention. The nucleic acid molecule (typically an in vitro, isolated or recombinant nucleic acid molecule) preferably encodes any one of the heavy chain variable regions as depicted in FIG. 3 or a heavy chain variable region as depicted in FIG. 3 having 1, 2, 3, 4 or 5 amino acid insertions, deletions, substitutions or combination thereof. In a preferred embodiment the nucleic acid molecule comprises a sequence as depicted in FIG. 3. The nucleic acid molecule preferably uses codons that are optimized for expression in the antibody producing cell that is to be used. Preferably the nucleic acid encoding a heavy chain variable region as depicted in FIG. 3 or a heavy chain variable region as depicted in FIG. 3 having 1, 2, 3, 4 or 5 amino acid insertions, deletions, substitutions or combination thereof is codon optimized for expression in a human cell preferably Per.C6TM: or a Chinese hamster, preferably CHO. The invention further provides a nucleic acid sequence that codes for the mentioned heavy chain variable region together with a heavy chain constant region of FIG. 2.

A nucleic acid molecule as used in the invention is typically but not exclusively a ribonucleic acid (RNA) or a deoxyribonucleic acid (DNA). Alternative nucleic acids are available for a person skilled in the art. A nucleic acid molecule according to the invention is for instance comprised in a cell. When said nucleic acid molecule is expressed in said cell, said cell can produce an antibody according to the invention. Therefore, the invention in one embodiment provides a cell comprising an antibody according to the invention and/or a nucleic acid molecule according to the invention. An antibody is produced when said cell produces a heavy chain and a light chain. Provided is a cell that can produce an antibody of the invention. The cell preferably comprises a nucleic acid molecule that encodes an antibody heavy chain that comprises an antibody heavy chain variable region that, when combined with a common light chain, can bind said first membrane protein. Said cell preferably further comprises a nucleic acid molecule that encodes an antibody heavy chain that comprises an antibody heavy chain variable region that, when combined with a common light chain, can bind said second membrane protein. Said cell preferably further comprises a nucleic acid molecule that codes for a common light chain. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Also provided is a cell that comprises one or more nucleic acid molecules that alone or together encode an antibody of the invention. The one or more nucleic acid molecules are expressible nucleic acid molecules meaning that they contain the in cis required signals for RNA transcription and translation of protein coding domains. Preferably said cell (typically an in vitro, isolated or recombinant cell) produces said antibody. In a preferred embodiment said cell is a hybridoma cell, a Chinese hamster ovary (CHO) cell, an NS0 cell or a PER- C6TM cell. In a particularly preferred embodiment said cell is a CHO cell. Further provided is a cell culture that comprises a cell according to the invention. Various institutions and companies have developed cell lines for the large scale production of antibodies, for instance for clinical use. Non-limiting examples of such cell lines are CHO cells, NS0 cells or PER.C6TM cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy chain as depicted in FIGS. 3, 1 and 2. Preferably said nucleic acid molecule comprises a sequence as depicted in FIGS. 1 and 2.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or any other cell type known in the art for its suitability for antibody production for clinical purposes, in particular for the production of antibodies used for administration in humans. In a particularly preferred embodiment said cell is a human cell, preferably a cell that is transformed by an adenovirus E1 region or a functional equivalent thereof. A preferred example of such a cell line is the PER.C6TM cell line or equivalent thereof. In a particularly preferred embodiment said cell is a CHO cell or a variant thereof, preferably a variant that makes use of a Glutamine synthetase ((GS) vector system for expression of an antibody.

The invention further provides a pharmaceutical composition comprising one or more antibodies or variants thereof according to the invention. The pharmaceutical composition preferably comprises a preferably pharmaceutically acceptable excipient or carrier.

An antibody or variant thereof of the invention may further comprise a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800: IRDye 680RD: IRDye 680LT: IRDye 750; IRDye 700DX: IRDye 800RS IRDye 650: IRDye 700 phosphoramidite: IRDye 800 phosphoramidite (LI-COR USA: 4647 Superior Street: Lincoln, Nebraska).

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in range of the dosing regimen of Nivolumab. The dosage can also be lower.

An antibody or variant thereof and in particular a bispecific antibody or a variant thereof according to the invention may have fewer side effects than a combination of bivalent monospecific antibodies with the variable domains. An antibody or bispecific antibody or a functional part, derivative and/or analogue thereof according to the invention has less immune-related toxicity than a combination of bivalent monospecific antibodies with the variable domains. The antibody or bispecific antibody reduces safety liabilities in patients. Combinations of antibodies that block inhibitory and/or costimulatory molecules benefit patients that do not respond to existing immunotherapies. However, dual blockade of immuno-modulatory receptors (iMODs) has been shown to increase immune-related toxicity. An antibody or variant thereof and in particular a bispecific antibody or a variant thereof according to the invention is suited to address dual blockade of iMODs, as they can exert functional activities that cannot be reproduced by monoclonal antibody combinations, and can more selectively target specific cell populations, which reduces safety liabilities in patients.

The antibodies were produced as bispecific antibodies by cloning them into complementary expression vectors that contain mutations in the CH3 region that drives heterodimerization of heavy chains. Many bispecific antibodies were produced at small scale and tested in binding and functional assays on cancer cell lines. An antibody of the invention, particularly a bispecific antibody of the invention can combine low toxicity profiles with high efficacy. An antibody of the invention can be useful in various types and lines of immune targeted therapies. An antibody of the invention can have an increased therapeutic window when compared to an antibody that binds the same antigen(s) with both arms.

Further provided is a use of a bispecific antibody according to the invention or a functional part, derivative and/or analogue thereof, for the preparation of a medicament for the treatment or prevention of aberrant cells, a tumor and/or the formation of metastases. The tumor from which said metastases originate is preferably a tumor that is positive for PD-L1. PD-L2 and/or Galectin-9.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1.

For the purpose of clarity and a concise description features are described herein as part of the same or separate embodiments, however, it will be appreciated that the scope of the invention may include embodiments having combinations of all or some of the features described.

Also provided is a method for the treatment of an individual that has a cancer, the method comprising administering a protein of the invention or a bispecific antibody of the invention to the individual in need thereof.

The invention further provides a protein of the invention or a bispecific antibody of the invention, for use in the treatment of an individual that has cancer.

The antibody or variant thereof of the invention preferably comprises a variable domain that can bind to an extra cellular part of PD-1 and comprises a heavy chain variable region with a CDR3 region that comprises the amino acid sequence of the CDR3 of a variable heavy chain region of one of the VH depicted for MF6076; MF6236; MF6256; MF6226; MF6930; MF6932; MF6935; MF6936; MF6972; MF6974: or MF6982: preferably MF6226: MF6256; or MF6930 in FIG. 3. Said variable domain that binds PD-1 preferably comprises a heavy chain variable region comprises a heavy chain variable region with a CDR1. CDR2 and CDR3 region that comprises the amino acid sequence of the CDR1, CDR2 and CDR3 of a variable heavy chain region of one of the VH depicted for MF6076: MF6236; MF6256: MF6226; MF6930; MF6932: MF6935; MF6936; MF6972: MF6974; or MF6982; preferably MF6226; MF6256: or MF6930 in FIG. 3.

The antibody or variant thereof preferably comprises a variable domain that can bind to an extra cellular part of PD-1 and comprises a heavy chain variable region that comprises the amino acid sequence of the variable heavy chain region as depicted for MF6076; MF6256: MF6226; MF6930; MF6932: MF6935; MF6936; MF6972; MF6974; or MF6982: preferably MF6226: MF6256: or MF6930 (as depicted in FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the VH as depicted for the indicated MF.

The antibody or variant thereof preferably comprises a variable domain that can bind to an extra-cellular part of TIM-3 and that comprises a heavy chain variable region with a CDR3 region that comprises the amino acid sequence of the CDR3 region of the variable heavy chain region as depicted for MF7676; MF7677; MF7678; or MF7679 of FIG. 3. Said variable domain that binds TIM-3 preferably comprises a heavy chain variable region comprises a heavy chain variable region with a CDR1, CDR2 and CDR3 region that comprises the amino acid sequence of the CDR1, CDR2 and CDR3 of a variable heavy chain region of one of the VH depicted for MF7676; MF7677: MF7678; or MF7679 of FIG. 3.

The antibody or variant thereof preferably comprises a variable domain that can bind to an extra cellular part of TIM-3 and comprises a heavy chain variable region that comprises the amino acid sequence of the variable heavy chain region as depicted for MF7676; MF7677: MF7678; or MF7679 (of FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the indicated MF.

The invention is further explained in the following examples. These examples do not limit the scope of the invention, but merely serve to clarify the invention.

BRIEF DESCRIPTION OF THE DRAWINGS

FIG. 1. Common light chain used in mono- and bispecific IgG. FIG. 1A: Common light chain amino acid sequence. FIG. 1B: Common light chain variable domain DNA sequence and translation (IGKV1-39/jk1). FIG. 1C: Common light chain constant region DNA sequence and translation. FIG. 1D: IGKV1-39/jk5 common light chain variable domain translation. FIG. 1E: V-region IGKV1-39A FIG. 2. IgG heavy chains for the generation of bispecific molecules.

FIG. 2A: VH gene. FIG. 2B: CH1 region. FIG. 2C: hinge region. FIG. 2D: CH2 region. FIG. 2E: CH2 region containing L235G and G236R silencing substitutions.

FIG. 2F: CH3 domain containing substitutions L351K and T366K (KK). FIG. 2G; CH3 domain containing substitutions L351D and L368E (DE)

FIG. 3. Amino acid sequences of heavy chain variable regions:

FIG. 3A. heavy chain variable regions of PD-1 specific clones

FIG. 3B. heavy chain variable regions of TIM-3 specific clones

The notation MF refers to a fab containing a heavy chain variable region as depicted and a common light chain. The amino acid sequence of the light chain is indicated in FIG. 1A. The underlined sequences indicate per amino acid sequence respectively the CDR1, the CDR2 and the CDR3 region.

Figure 4:
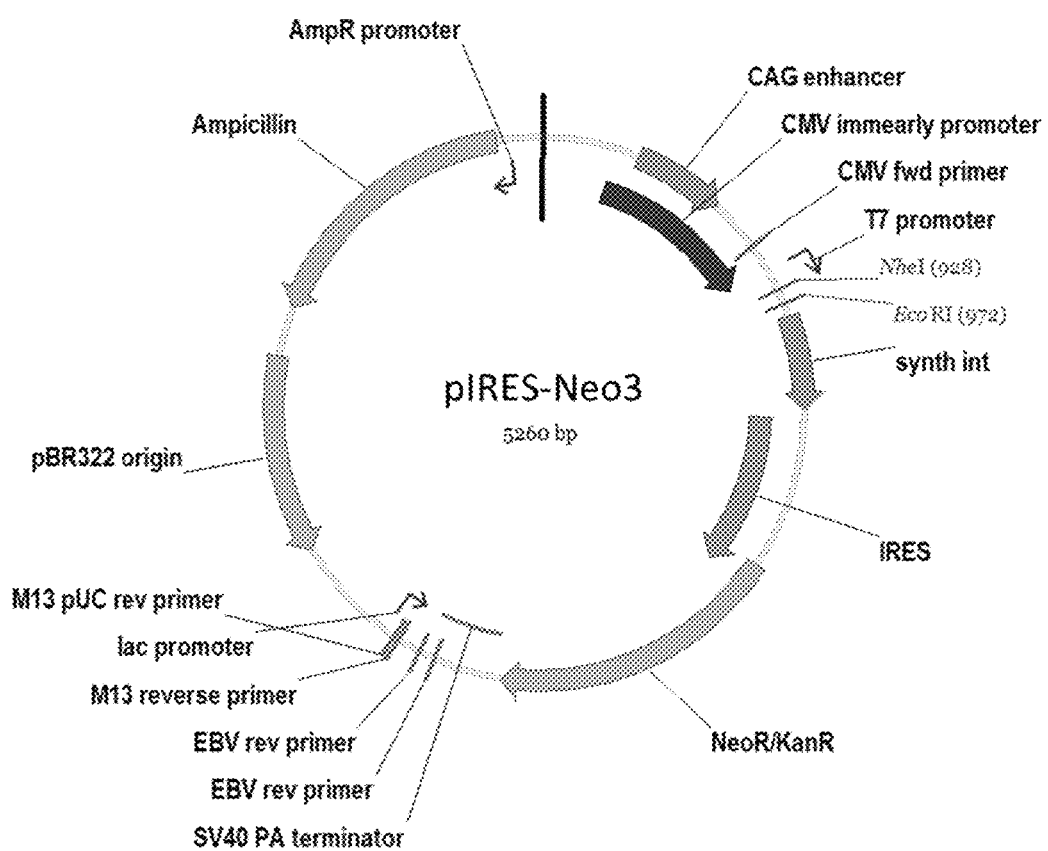

FIG. 4. Vector map and features of pIRES-Neo3 (MV1363).

Figure 5:
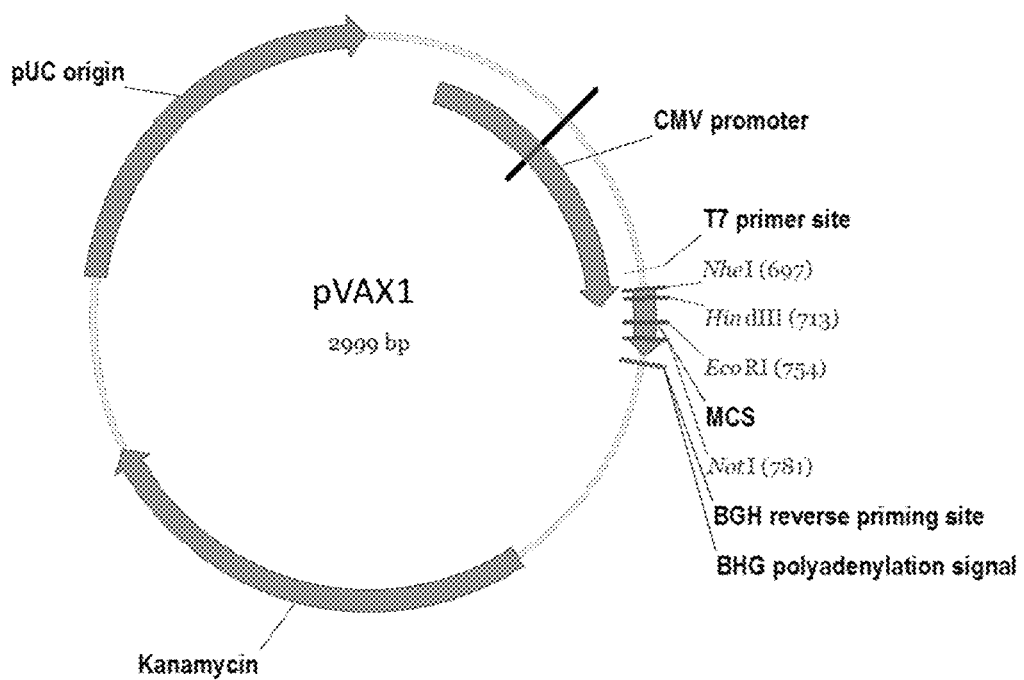

FIG. 5. Vector map and features of pVAX1.

Figure 6:
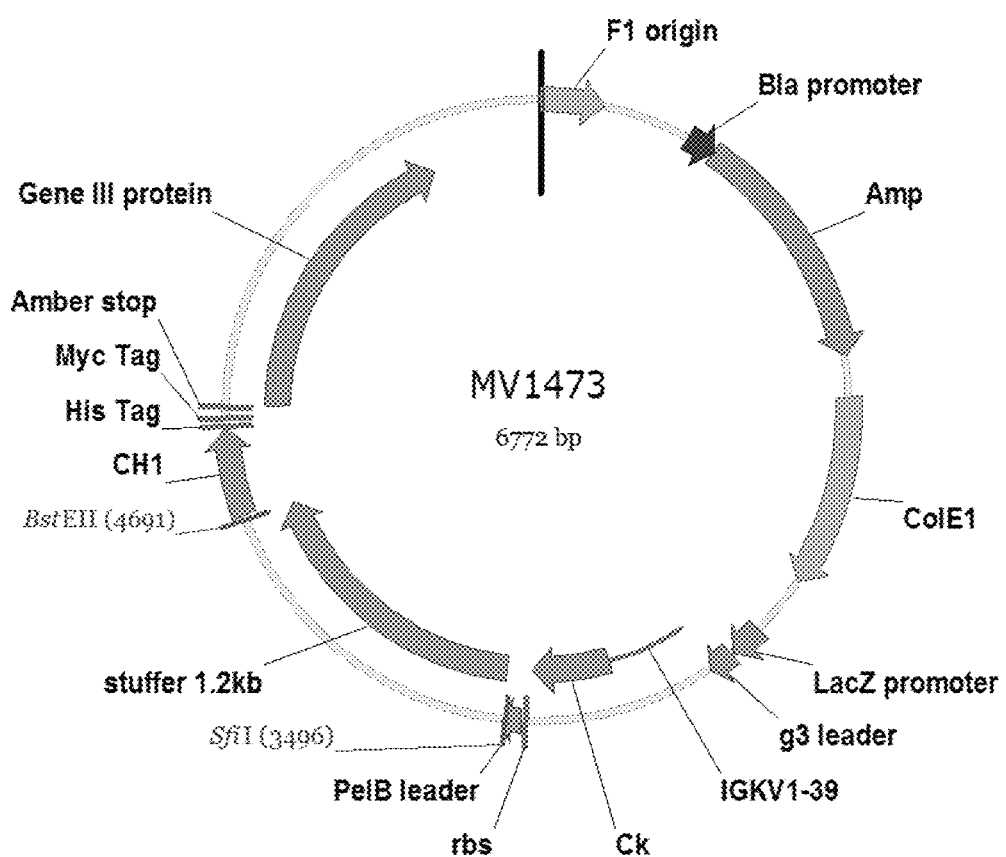

FIG. 6. Vector map and features of the phagemid vector MV1473 used to generate 'immune' phage display libraries.

Figure 7:
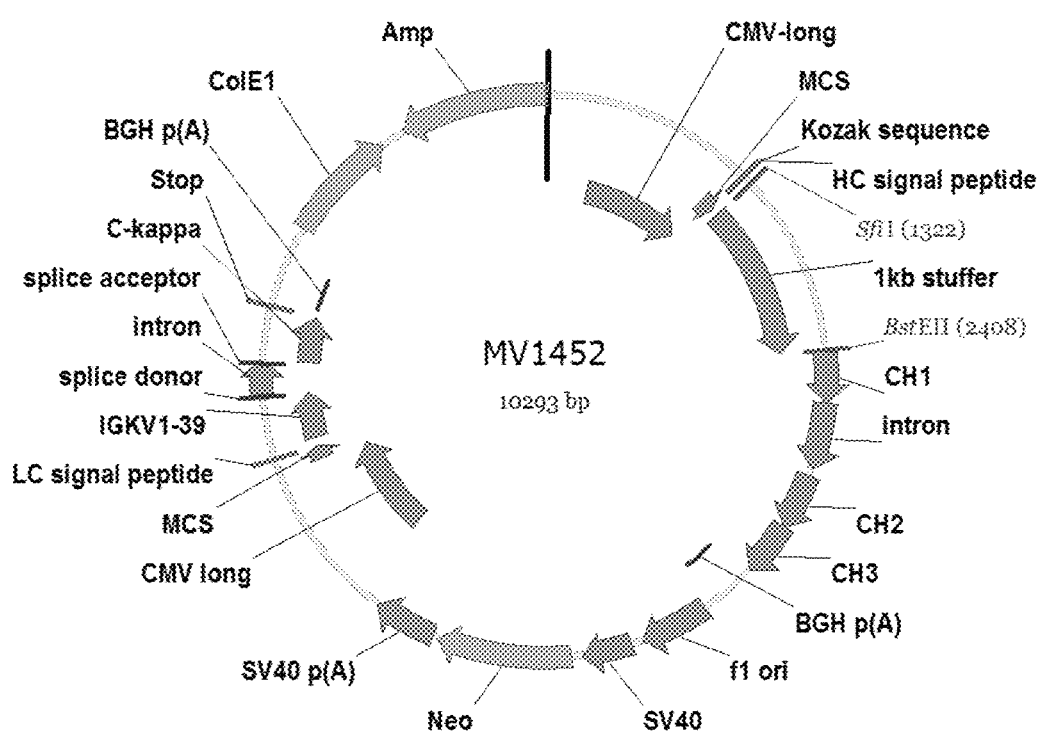

FIG. 7. Vector map and features of the IgG expression vector MV1452, that was used for expression of the PD-1 and PD-L1 specific Fab arms in the KK-variant heavy chain for bispecific IgG generation.

FIG. 8. Amino acid sequence of the VH gene that is tetanus toxin specific when combined with the common light chain as MF1337, and that is present in the DE-variant heavy chain that was used to generate PD-L1×TT and PD-1×TT bispecific IgG molecules. The underlined sequences indicate per amino acid sequence respectively the CDR1, the CDR2 and the CDR3 region.

Figure 9:
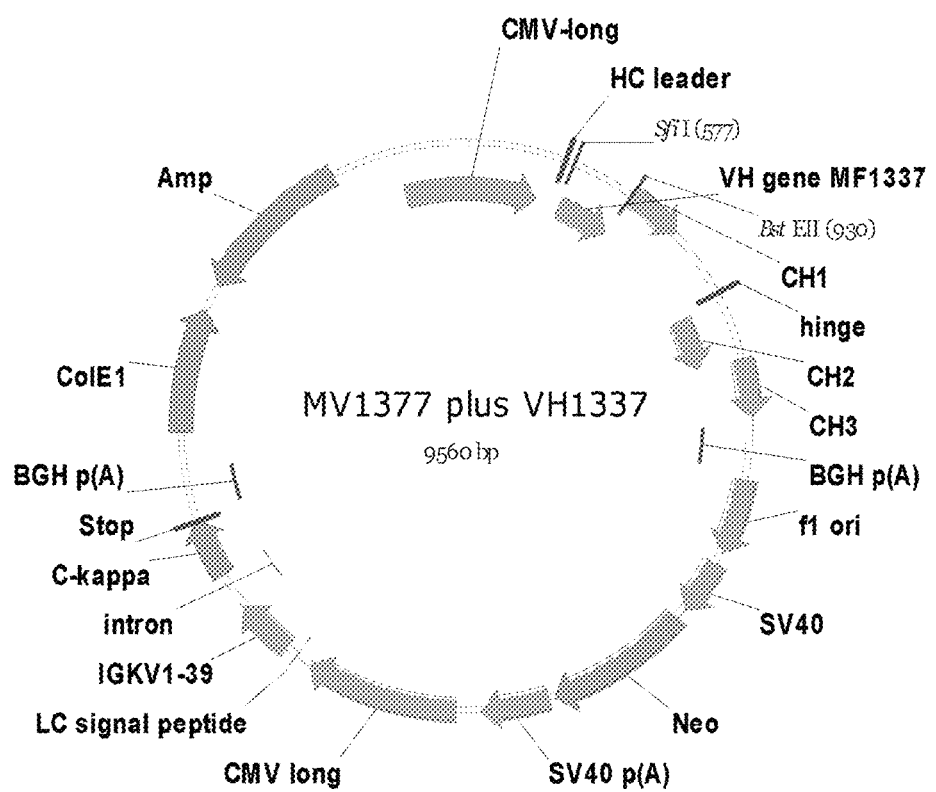

FIG. 9. Vector map and features of the IgG expression vector MV1377, that was used for expression of the TT specific Fab arm MF1337 in the DE-variant heavy chain for bispecific IgG generation.

Figure 10:
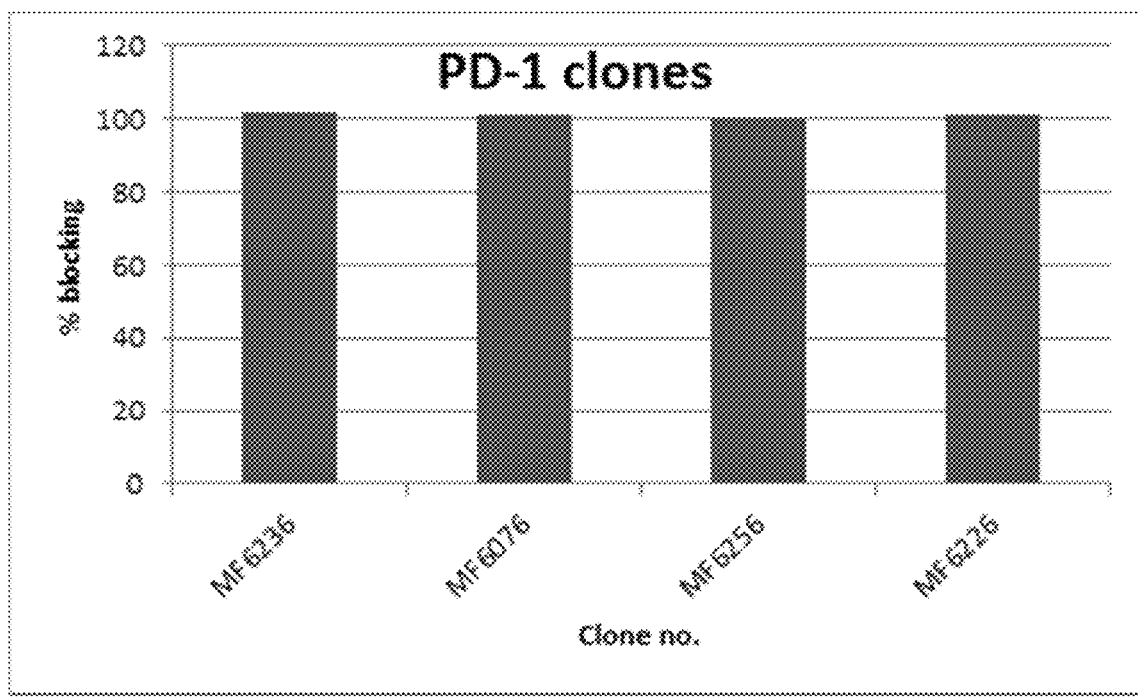

FIG. 10. PD-1/PD-L1 blocking assay

Assessment of the capacity of the anti-PD-1 antibody panel to block the interaction of PD-L1 to coated PD-1 at a concentration of 10 µg/ml bispecific IgG. Data are normalized to data obtained with the bivalent benchmark PD-L1 antibody MPDL3280A at a concentration of 10 µg/ml (100% blocking). A representative example is shown of the PD-1 panel. Maximum binding (normalized to 0% blocking) was established by incubation with a non-PD-1/PD-L1 specific human isotype antibody. All PD-1 variable domains comprising MF sequences depicted in FIG. 3 and not represented here block the PD-1/PD-11 interaction >70%.

Figure 11:
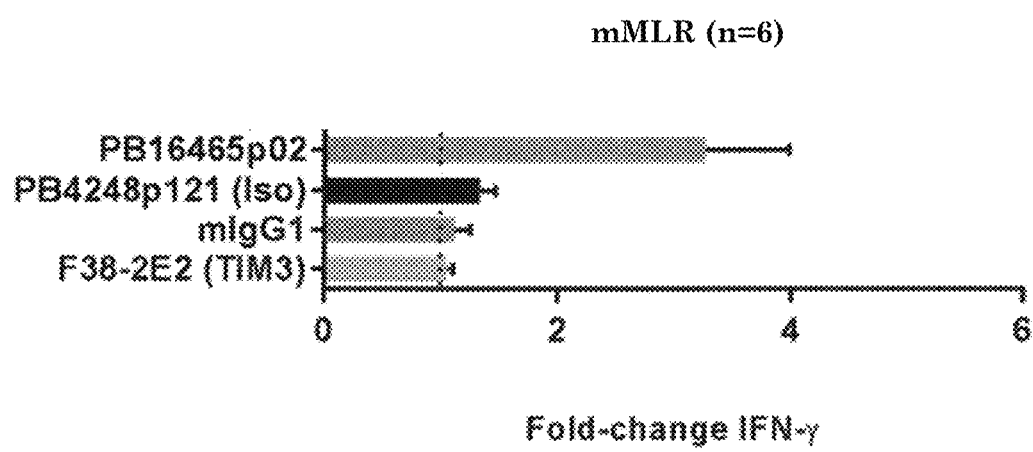

FIG. 11. Effect of test antibodies on IFN-γ production in allogeneic mMLR. Mo-DCs were prepared from CD14+ monocytes cultured for 7 days. Immature DCs were used on day 7 and mature DCs were generated by culturing for a further 3 days in maturation medium before being cultured together with T cells isolated by negative selection and test antibody for 4 days (mMLR). IFN-γ was measured in culture supernatants by ELISA. Data are normalized to vehicle control. Six separate MLRs were performed.

EXAMPLES

As used herein "MFXXXX" wherein X is independently a numeral 0-9, refers to a Fab comprising a variable domain wherein the VII has the amino acid sequence identified by the 4 digits. Unless otherwise indicated the light chain variable region of the variable domain typically has a sequence of FIG. 1A, typically 1B. "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The variable region of the heavy chains (VH) differs and typically also the CH3 region, wherein one of the heavy chains has a KK mutation of its CH3 domain and the other has the complementing DE mutation of its CH3 domain (see for reference PCT/NL2013/050294 (published as WO2013/157954).

Example: 1

Generation of Materials for Selection and Screening
Culturing of Cell Lines

Freestyle 293F cells (cat. no. p/n51-0029) were obtained from Invitrogen and routinely maintained in 293 FreeStyle medium. HEK293T (cat. no. ATCC-CRL-11268) cells were purchased from ATCC and routinely maintained in DMEM/F12 (Gibco) supplemented with L-Glutamine (Gibco) and FBS (Lonza), and CHO-S (cat. no. 11619-012) cell lines were purchased from Gibco and routinely maintained in Freestyle CHO expression medium (Invitrogen) supplemented with L-glutamine.

Generation of PD-1 and TIM-3 Expression Vectors for Immunization, and for Generation of Stable Cell Lines and Transient Transfections Full length cDNA of each target including unique restriction sites for cloning and kozak consensus sequence for efficient translation was either synthetized, or obtained via PCR amplification on a commercially available expression construct, containing the target cDNA, with specific primers that introduced unique restriction sites for cloning and kozak consensus sequence for efficient translation. The cDNA of each target was cloned into a eukaryotic expression construct such as pIRES-Neo3 (Clontech: FIG. 4) or pVAX1 (Thermo Fisher Scientific: FIG. 5) via NheI/EcoRI, resulting in pIRES-Neo3_[TARGET_NAME] and pVAX1_[TARGET_NAME], respectively. The insert sequences were verified by comparison with NCBI Reference amino acid sequences. The pIRES-Neo3 constructs were used for generation of stable cell lines and transient transfections. The pVAX1 constructs were used for immunization purposes. See TABLE 1 for an overview of the names of the resulting constructs.

Amino acid sequence full length huPD-1 insert (both in pIRES-Neo3 and pVAX1) for expression on the cell surface (Identical to GenBank: NP_005009.2):

```
                                           (SEQ ID NO: 1)
MQIPQAPWPVVWAVLQLGWRPGWFLDSPDRPWNPPTFSPALLVVTEGD

NATFTCSFSNTSESFVLNWYRMSPSNQTDKLAAFPEDRSQPGQDCRFRVTQ

LPNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTIG

ARRTGQPLKEDPSAVPVFSVDYGELDFQWREKTPEPPVPCVPEQTEYATIV

FPSGMGTSSPARRGSADGPRSAQPLRPEDGHCSWPL
```

Of which:

```
                                           (SEQ ID NO: 2)
MQIPQAPWPVVWAVIALGWR: signal peptide .
```

```
                                           (SEQ ID NO: 3)
PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVPTAHPSPSPR-
PAGQFQTLV:

ECD of huPD-1 .
```

```
                                           (SEQ ID NO: 4)
VGVVGGLLGSLVLLVWVLAVI: Predicted TM region.
```

```
                                           (SEQ ID NO: 5)
CSRAARGTIGARRTGQPLKEDPSAVPVFSVDYGELDFQWREKTPEPPVPC

VPEQTEYATIVFPSGMGTSSPARRGSADGPRSAQPLRPEDGHCSWPL:

Intracellular tail .
```

Amino acid sequence full length macaque (*Macaca fascicularis*) PD-1 insert (both in pIRES-Neo3 and pVAX) for expression on the cell surface (Identical to GenBank: ABR15751.1):

```
                                           (SEQ ID NO: 6)
MQIPQAPWPVVWAVLQLGWRPGWFLESPDRPWNAPTFSPALLLVTEGDN

ATFTCSFSNASESEVLNWYRMSPSNQTDKLAAFPEDRSQPGQDCRERVTR

LPNGRDFHMSVVRARRNDSGTYLCGAISLAPKAQIKESLRAELRVTERRA

EVPTAHPSPSPRPAGQFQALVVGVVGGLLGSLVLINWVLAVICSRAAQGT

IEARRTGQPLKEDPSAVPVESVDYGELDFQWREKTPEPPAPCVPEQTEYA

TIVEPSGLGTSSPARRGSADGPRSPRPLRPEDGHCSWPL
```

Of which:

```
                                           (SEQ ID NO: 7)
MQIPQAPWPVVWAVLQLGWR: signal peptide .
```

```
                                           (SEQ ID NO: 8)
PGWFLESTDRPWNAPTFSPALLLVTEGDNATFTCSFSNASESTVLNWYR

MSTSNIQTDKLAAFPEDRSQPNDCRFRYTELPN-
GRDFHMSVVRARRNDSGT

YLCGAISLAPKAQIKESLRAELRVTERRAEVPTAHRSPSPR-
PAGQFQALV:

EC,D of maPD-1 .
```

```
                                           (SEQ ID NO: 9)
VGVVGGLLGSLVLINIVVLAVI: Predicted TM region.
```

```
                                          (SEQ ID NO: 10)
CSRAAQGTIEARRTGQPLKEDPSAVPVESVDYGELDFQWREKTPEPPAPC

VPEQTEYATIVFPSGLGTSSPARRGSADCIPRSTRPLRPEDGHCSWPL:

Intracellular tail .
```

Amino acid sequence full length human TIM-3 insert (both in pIRES-Neo3 and pVAX1) for expression on the cell surface (Identical to GenBank: AAH63431.1):

```
                                          (SEQ ID NO: 11)
MFSHLPFDCVLLLLLLLLLTRSSEVEYRAEVNNAYLPCFYTPAAPGNLVP

VCWGKGACPVFECGNVVLRTDERDVNYWTSRYWLNGDFRKGDVSLTIENVT

LADSGIYCCRIQIPGIMNDEKFNLKLVIKPAKVTPAPTLQRDFTAAFPRML

TTRGHGPAENTLGSLPDINLTQISTLANELRDSRLANDLRDSGATIRIGIY
```

-continued

IGAGICAGLALALIFGALIFKWYSHSKEKIQNLSLISLANLPPSGLANAVA

EGIRSEENIYTIEENVYEVEEPNEYYCYVSSRNPSQPLGCRFAMP

Of which:

(SEQ ID NO: 12)
MFSHLPFDCVLLLLLLLLTRS: signal peptide.

(SEQ ID NO: 13)
SEVEYRAEVGQNAYLPCFYTPAAPGNLVPVCWGKGACPVFECGNVVLRT

DERDVNYWTSRYWLNGDFRKGDVSLTIENVTLADSGIYCCRIQIPGIMNDE

KFNLKLVIKPAKVTPAPTLQRDFTAAFPRMLTTRGHGPAETQTLGSLPDIN

LTQISTLANELRDSRLANDLRDSGATIRIG: ECD.

(SEQ ID NO: 14)
IYIGAGICAGLALALIFGALI: Predicted TM region.

(SEQ ID NO: 15)
FKWYSHSKEKIQNLSLISLANLPPSGLANAVAEGIRSEENIYTIEENVYE

VEEPNEYYCYVSSRQQPSQPLGCRFAMP: Intracellular tail.

Amino acid sequence full length macaque TIM-3 (*Macaca fascicularis*) insert (both in pIRES-Neo3 and pVAX1) for expression on the cell surface (Identical to GenBank: EHH15470:3.1):

(SEQ ID NO: 16)
MFSHLPFDCVLLLLLLLLTRSSEVEYIAEVGQNAYLPCSYTPAPPGNLVPV

CWGKGACPVFDCSNVVLRTDNRDVNDRTSGRYWLKGDFHKGDVSLTIENVT

LADSGVYCCRIQIPGIMDEKHNVKLVVIKPAKVTPAPTLQRDLTSAFPRML

TTGEHGPAETQTPGSLPDVNLTVSNFFCELQIFTLTNELRDSGATIRTAIY

IAAGISAGLALALIFGALIFKWYSHSKEKTQNLSLISLANIPPSGLANAVA

EGIRSEENIYTIEEDVYEVEEPNEYYCYVSSGQQPSQPLGCRVAMP

Of which:

(SEQ ID NO: 17)
MFSHLPFDCVLLLLLLLLTRS: signal peptide.

(SEQ ID NO: 18)
SEVEYIAEVNNAYLPCSYTPAPPGNLVPVCWGKGACPVFDCSNVVLRTD

NRDVNDRTSGRYWLKGDFHKGDVSLTIENVTLADSGVYCCRIQIPGIMDE

KHNVKLVVIKPAKVTPAPTLQRDLTSAFPRMLTTGEHGPAETQTPGSLPD

VNLTVSNFFCELQIFTLTNELRDSGATIRTA: ECD.

(SEQ ID NO: 19)
IYIAAGISAGLALALIFGALI: Predicted TM region (SEQ ID NO: 20)
FKWYSHSKEKTQNLSLISLANIPPSGLANAVAEGIRSEENIYTIEEDVYE VEEPNEYYCYVSSGQQPSQPLGCRVAMP: Intracellular tail.

Generation of Stable Cell Lines Expressing PD-1 and TIM-3 pIRES-Neo3_[TARGET_NAME] expression constructs (TABLE 1) were used to generate C10-S or Freestyle 293F clones stably expressing the respective proteins. Constructs were transiently transfected in CHO-S and Freestyle 293F cells using lipofectamine transfection, and screened by FACS using antibodies reacting with the respective proteins. After confirmation of expression, transiently transfected cells were seeded in limiting dilution and cultured under selection pressure relevant for the used expression construct to obtain stable cell clones. After 2-3 weeks of selection, clones were screened by FACS. The selected clones were expanded by serial passage, retested in FACS and frozen to −150° C. The names of clones that stably express the heterologous proteins are CHO-S_[TARGET_NAME] cells or Freestyle 293F_[TARGET_NAME] cells. See TABLE 1 for an overview of the constructs used to generate the stable cell lines and their resulting name.

Example 2

Immunization. Selection and Screening
Mice Used for Immunizations

For generation of human antibodies binding to huPD-1 and huTIM-3, mice transgenic for the human VK1-39 light chain (common light chain mice, see WO2009/157771) and for a human heavy chain (HTC) minilocus (comprising a selection of human V gene segments, all human Ds and all human Js) were immunized. These mice are referred to as 'MeMo®' mice. Mice were immunized with either recombinant protein antigen, or DNA encoding the protein antigen as briefly described below.

Protein Immunizations

'MeMu®' mice were immunized by subcutaneous injections with recombinant protein and Gerbu adjuvant MM (Gerbu Biotechnik; cat. no. 3001). Recombinant huPD-1-Fc (R&D; cat. no. 1086-PD), huTIM-3-Fc (R&D; cat. no. 2365-TM) and maTIM-3-Fc (R&D: cat. no. 7914-TM) were used for immunizations. Mice were immunized with 40 μg recombinant protein in PBS mixed with 40 μl of adjuvant in a total volume of 100 μl. Subsequently mice were boosted on day 14 and 28 with 20 μg of recombinant protein in PBS together with 20 μl of adjuvant in a total volume of 50 μl. Mouse serum was collected at day 35 to determine serum titers. Mice with low serum reactivity against the human and/or macaque target received additional cycles of booster immunizations with recombinant human or macaque protein antigen and serum analyses. Each cycle consisted of two weekly immunizations using to 20 μg of recombinant protein in 50 μl PBS followed one week later by serum collection for titer analysis. Mice showing high serum titers against the human and macaque target received a final boost immunization consisting of daily injections with 20 μg of recombinant protein in 50 μl PBS on three consecutive days. One day after the final injection mouse lymphoid tissue was collected.

DNA Immunizations

MeMo®' mice were immunized by DNA tattooing using a micropigmentation device. DNA tattoo immunizations were performed with 20 μg plasmid DNA encoding the target antigen (pVAX1_[TARGET_NAME], TABLE 1). Mice were immunized with DNA encoding the human target. Mice were immunized at day 0, 3, 6, 14, 17, 28 and 31. Mouse serum was collected at day 35 to determine serum titers. Mice with low serum reactivity against the human and/or macaque target received additional cycles of booster immunizations with human DNA antigen, and serum analyses. Each cycle consisted of two weekly DNA immunizations followed one week later by serum collection for titer analysis. Mice showing strong serum reactivity against cells expressing the human and macaque target received a final boost immunization followed after 3 days by collection of lymphoid tissue.

Determination of Serum Titers

Serum titers were determined by FACS analysis using cell lines expressing the human and macaque target antigens.

Generation of Synthetic Phage Fab Libraries

Synthetic libraries were constructed based on a repertoire of germline human VH genes that were selected for frequent use in natural repertoires and canonical sequence diversity. Synthetic HCDR3 regions were added to these VH genes using PCR. This was done using forward primers that anneal to framework 1 of the VH genes and include a SfI restriction site for cloning. Reverse primers included sequences to anneal to framework 3 of the VH genes, followed by randomized sequences to encode HCDR3 diversity and a framework 4 encoding sequence also containing a BstEII and XhoI restriction site for cloning. Synthetic CDR3 regions were either completely random or encoded a more restricted diversity based on the frequency of use of amino acid residues at certain positions within the HCDR3.

PCR products encoding the VH genes were cloned into phage display vectors in fusion with phage M13 gene 3 protein using aforementioned restriction enzymes and also containing a common light chain encoding gene. Large scale ligation and transformation of E'coli TG1 resulted in large libraries of synthetic Fab fragments displayed on phage which were used for panning on antigens or cells to identify antigen-specific Fab fragments.

Generation of 'Immune' Phage Fab Libraries by RT-PCR from Tissues of Immunized Mice Spleen and draining lymph nodes were removed from mice for which a significant humoral response was observed against the respective target proteins.

Single cell suspensions were generated from both spleen and inguinal lymph nodes and subsequently these tissues were lysed in Trizol LS Reagent (Thermo Scientific c #10296028) and stored at −80° C. until use.

From successfully immunized mice, the inguinal lymph nodes were used for the construction of 'immune' phage antibody repertoires. RNA was extracted from the single cell suspensions of the lymphoid tissue, 1 µg of total RNA was used in a RT reaction using an IgG-CH1 specific primer. The resulting cDNA was then used to amplify the polyclonal pool of VH-encoding cDNA using in-house adapted VH-specific primers essentially as described in Marks et al. (J Mol Biol. 1991 Dec. 5; 222(3):581-97). The resulting PCR product was then cloned in a phagemid vector (FIG. 6) for the display of Fab fragments on phage, as described in de Haard et al. (J Biol Chem. 1999 Jun. 25:274(26):18218-30) with the exception that the light chain (FIGS. 1A and 1B) was the same for every antibody and was encoded by the vector. After ligation, the phagemids were used to transform E. coli TG1 bacteria and transformed bacteria were plated onto LB-agar plates containing ampicillin and glucose. All phage libraries contained >4×10$^5$ transformants and had an insert frequency of >90%. Bacteria were harvested after overnight growth and used to prepare phage according to established protocols (de Haard et al., J Biol Chem. 1999 Jun. 25:274(26):18218.30).

Selection of Phage Carrying Fab Fragments Specifically Binding to Human Target Protein from Synthetic And 'Immune' Phage Fab Libraries Using Recombinant Proteins The phage Fab libraries that were generated were used to select target specific Fabs using phage display on directly coated recombinant proteins. For PD-1, huPD-1-Fc (R&D; cat. no. 1086-PD) and huPD-1 biotin (BPS bioscience; cat. no. 71109) were used. For TIM-3, huTIM-3-His (CreativeBiomart: cat. no. HAVCR2-3166H), huTIM-3-Fc (R&D; cat. no. 2365-TM) and maTIM-3-Fc (R&D; 7914-TM) were used.

For selections with non-biotinylated recombinant protein ('panning selections'), proteins were coated onto the wells of a MAXISORP™ ELISA plate. The MAXISORP™ ELISA plates were blocked with 4% dried skimmed milk (Marvel) in PBS. Phage Fab libraries were also blocked with 4% Marvel and, when Fc tagged recombinant protein was used, also with excess of human IgG to deplete for Fc region binders prior to the addition of the phage library to the coated antigen.

Incubation of the phage library with the coated protein was performed for 1.5 hrs at room temperature under shaking conditions. Plates or tubes were then washed fifteen times with 0.05% Tween-20 in PBS followed by 5 times washing with PBS. Bound phage were eluted for 20 minutes using trypsin, after which trypsin was neutralized with AEBSF trypsin inhibitor (Sigma).

For selections with biotinylated protein ('in-solution selections'), neutravidin was coated onto the well of a MAXISORP™ ELISA plate. The MAXISORP™ ELISA plates were blocked with 1% casein in PBS. In parallel, biotinylated protein and phage Fab libraries were blocked for 30 minutes in 0.5% casein in PBS, containing an excess of human IgG, in separate Eppendorf tubes. Thereafter, the blocked phage and biotinylated protein were mixed and incubated for 2 hours at room temperature. The mixture was thereafter added to the neutravidin coated wells for 20 minutes to capture the phage Fab particles that were bound to biotinylated protein. Plates were then washed fifteen times with 0.05% Tween-20 in PBS followed by 5 times washing with PBS. Bound phage were eluted for 20 minutes using trypsin, after which trypsin was neutralized with AEBSF trypsin inhibitor (Sigma).

The eluates of both selection strategies ('panning and in-solution') were added to E. coli TG-1 and incubated at 37° C. for phage infection. Subsequently infected bacteria were plated on agar plates containing Ampicillin and glucose, and incubated at 37° C. overnight. Single clones from the selection outputs were screened for target binding in ELISA or FACS depending on the target.

For selections with synthetic phage Fab libraries, a second round selection was performed after rescue of the first round selection output using the same protocol as outlined above for the first round selection. All three selection antigens used for TIM-3 1$^{st}$ round selections, were also used in the second round selections.

Selection of Phage Carrying Fab Fragments Specifically Binding to Human Target from 'Immune' Phage Fab Libraries Using Cells Stably Expressing the Target Protein Phage Fab libraries that were generated from target immunized mice were selected using phage display on cells expressing the respective target. The stable cell lines expressing PD-1 or TIM-3 (Table 1) were used for 1$^{st}$ round selections. Cells were blocked with 10% FBS in PBS. After blocking, the rescued phage were incubated with blocked cells. Cells plus phage were incubated for 1 hr at 4° C. Washing the cells (5 times) was performed using 1 ml of 10% FBS in PBS. Bound phage were eluted using trypsin for 20 minutes, after which trypsin was neutralized with AEBSF trypsin inhibitor (Sigma). The eluate was added to E. coli TG-1 and incubated at 37° C. for phage infection. Subsequently, phage-infected bacteria were plated on agar plates containing ampicillin and glucose, and incubated at 37° C. overnight.

Screening for Target Specific Fab Clones in ELISA

Of single clones, soluble Fab or phage were prepared (J Mol Biol. 1991 Dec. 5;222(3):581-97; J Biol Chem. 1999 Jun. 25; 274(26):18218-30). Obtained soluble Fab or phage samples were diluted (1:5 or 1:10, respectively) in 4% dried skimmed milk (Marvel) in PBS (blockbuffer) and tested for binding in ELISA to wells coated with the same antigen as was used for selection.

Bound Fabs were detected by staining with an anti-myc antibody (Roche: cat. no. 11667203001) diluted 1:1000 in blockbuffer, followed by a HRP-conjugated anti-mouse IgG antibody (Jackson Immunoresearch; cat. no. 715-035-150) diluted 1:5000 in blockbuffer. Bound phage were detected by staining with a HRP-conjugated monoclonal anti-M13 antibody (GE healthcare; cat. no. 27-9421-01) diluted 1:5000 in blockbuffer.

After each antibody staining, wells were washed with PBS-T (PBS-0.05% v/v Tween 20). Bound secondary antibody was visualized by TMB/$H_2O_2$ staining and staining was quantified by means of $OD_{450\ nm}$ measurement. Clones were considered to bind the target when the OD450 nm was at least three times above the background signal obtained with a negative control Fab.

The VH-encoding cDNA's of all target-specific clones were sequenced. A selection of unique clones based on sequence identity and cluster analysis was then analyzed in FACS on binding to PD-L1 expressed on cells as described below for the clones obtained from the cell selection outputs.

Screening for Target Specific Fab Clones in FACS

Of single clones, selected on cells expressing the respective target, soluble Fab or phage were prepared as described (J Mol Biol. 1991 Dec. 5;222(3):581-97; J Biol Chem. 1999 Jun. 25; 274(26):18218-30). Fab samples were tested for binding in FACS to cells expressing the human and macaque target (Table 1) by incubation with a mix of 1:5 diluted Fab sample with 1:1000 diluted anti-myc antibody (Gentaur: cat. no. 04-CMYC-9E10) in FACS buffer (0.5% HI-FBS in PBS). Bound Fab/anti-myc complexes were detected by incubation with an APC-conjugated goat anti-mouse IgG antibody (BD Bioscience; cat. no. 550826) diluted 1:500 in FACS buffer.

Phage samples were tested for binding in FACS by diluting the phage samples 1:3 in blockbuffer and incubation with target expressing cells for 1 hour. Bound phage were detected by staining with a biotinylated anti-M13 antibody (Fitzgerald, cat. nr. 61R-M101ABTB62-FEZ. 1:125 in FACS buffer, 30 minutes on ice) and PE-labeled streptavidin (Invitrogen, cat. nr. SA1004-4; 1:400 in FACS buffer for 15 minutes on ice). After each antibody incubation, wells were washed three times with FACS buffer. Stained cells were analysed using a FACS Accuri C6 instrument (Becton and Dickinson). Clones were considered positive when the mean fluorescence intensity was at least three times above the background signal obtained with a negative control Fab.

Example 3

Characterization huTIM-3 and huPD-1 Specific Fab Clones in IgG Format Recloning Human TIM-3 and PD-1 Specific Fab to IgG Format A selection of unique clones, based on CDR3 sequence and VH germline differences, that bound human and macaque target protein expressed on cells, was then re-cloned to an IgG expression plasmid such as MV1452 (FIG. 7), which contained the common light chain (FIG. 1), using Sfi1-BstEII digestion and ligation of the pool of digested cDNA's according to standardized molecular biological techniques.

Expression of Bispecific IgG Containing a Human TIM-3 or Human PD-1 Specific Fab and a Tetanus Toxin Specific Fab Bispecific antibodies were generated by transient co-transfection of two plasmids encoding IgG with different VH1 domains, using a proprietary CH3 engineering technology to ensure efficient hetero-dimerisation and formation of bispecific antibodies. The common light chain present on both plasmids containing the heavy chain is also co-transfected in the same cell. In our co-pending applications (e.g. WO2013/157954 and WO2013/157953; incorporated herein by reference) we have disclosed methods and means for producing bispecific antibodies from a single cell, whereby means are provided that favor the formation of bispecific antibodies over the formation of monospecific antibodies. These methods can also be favorably employed in the present invention. Specifically, preferred mutations to produce essentially only bispecific full length IgG molecules are amino acid substitutions at positions 351 and 366. e.g. 1351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa (FIG. 2). It was previously demonstrated in our co-pending applications that the negatively charged DE-variant heavy chain and positively charged KK-variant heavy chain preferentially pair to form heterodimers (so-called 'DEKK' bispecific molecules). Homodimerization of DE-variant heavy chains (DE-DE homodimers) or KK-variant heavy chains (KK-KK homodimers) hardly occurs due to strong repulsion between the charged residues in the CH3-CH3 interface between identical heavy chains.

VH genes encoding the antibodies binding human TIM-3 and PD-1 described above were cloned into the MV1452 IgG expression vector encoding the positively charged CH3 domain. A tetanus toxin (TT) targeting antibody (FIG. 8) was cloned into the MV1377 IgG expression vector (FIG. 9) encoding the negatively charged CH3 domain. For expression of the TIM-3 and PD-1 antibody panel in IgG format, the entire panel was also cloned into the negatively charged CH3 domain vector to be able to produce bivalent TIM-3 or PD-1 IgG. Suspension growth-adapted 293F Freestyle cells were cultivated in T125 flasks on a shaker plateau until a density of $3.0 \times 10^6$ cells/ml. Cells were seeded at a density of $0.3$-$0.5 \times 10^6$ viable cells/ml in each well of a 24-deep well plate. The cells were transiently transfected with a mix of two plasmids encoding different antibodies, cloned into the proprietary vector system. Seven days after transfection, the cellular supernatant was harvested and filtered through a 0.22 µM filter (Sartorius). The sterile supernatant was stored at 4° C. until purification of the antibodies.

Purification of Bispecific IgG

Purification of IgG was performed on a small scale (<500 pig), using protein-A affinity chromatography. Small scale purifications were performed under sterile conditions in 24 well filter plates using filtration. First, the pH of the medium was adjusted to pH 8.0 and subsequently, IgG-containing supernatants were incubated with protein A Sepharose CL-4B beads (50% v/v) (Pierce) for 2 hrs at 25° C. on a shaking platform at 600 rpm. Next, the beads were harvested by filtration. Beads were washed twice with PBS pH 7.4. Bound IgG was then eluted at pH 3.0 with 0.1 M citrate buffer and the eluate was immediately neutralized using Tris pH 8.0. Buffer exchange was performed by centrifugation using multiscreen Ultracel 10 multiplates (Millipore). The samples were finally harvested in PBS pH 7.4. The IgG concentration was measured using Octet. Protein samples were stored at 4° C.

IgG Quantification Using Octet

To determine the amount of IgG purified, the concentration of antibody was determined by means of Octet analysis using protein-A biosensors (Forte-Bio, according to the suppliers recommendations) using total human IgG (Sigma Aldrich, cat. nr. 14506) as standard.

Specificity Analysis huTIM-3 and huPD-1 IgG

The antibodies (bispecific TIM-3×TT and PD-1×TT antibodies) were tested for binding in FACS to the stable cell lines expressing the relevant human and macaque orthologs (Table 1) and the wt cells. Therefore, cells were harvested and diluted to $10^6$ cells/ml in FACS buffer (PBS/0.5% BSA/0.5 mM EDTA). 1-2×$10^5$ cells were added to each well in a U-bottom 96 well plate. Cells were centrifuged for 2 minutes at 300 g at 4° C. Supernatant was discarded by inverting the plate(s). 50 µl of each IgG sample at a concentration of 10 µg/ml was added and incubated for 1H on ice. Cells were centrifuged once, supernatant was removed and cells were washed twice with 150 µl of FACS buffer. 50 µl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

Binning huPD-1 Specific Fab Arms Present in the PD-1×TT Bispecific IgG on Ligand Blocking Ability huPD-1 binding clones were tested for their ability to block the interaction of PD-L1 with PD-1. Therefore PD1-Fc (R&D systems; cat. no. 1086-PD) was coated to a maxisorp plate at 1 µg/ml. Coated wells were blocked with 4% BSA in PBS. Thereafter, 0.55 µg/ml biotinylated PD-L1 (BPS bioscience: cat. no. 71105) was added in the presence or absence of IgG in the range of 0.15 to 20 µg/ml. Bound biotinylated PD-L1 was detected with HRP-conjugated streptavidin (BD bioscience: cat. no. 554066) diluted 1:2000 in block buffer. After each incubation step, the ELISA plate was washed three times with PBS-T (PBS-0.05% v/v Tween 20). Bound streptavidin was visualized by TMB/$H_2O_2$ staining and staining was quantified by means of $OD_{450\ nm}$ measurement. Clones were considered to block the interaction of PD-1 with PD-L1 when the ELISA signal was reduced more than 70% at an IgG (PD-1×TT) concentration of 10 µg/ml, compared to a control in which a TT specific competition antibody was added. See FIG. 10 for the results obtained with a representative selection of the PD-1 antibody panel tested as PD-1×TT bispecific molecules.

Binning huTIM-3 Specific Fab Arms Present in the TIM-3×PD-1 IgG on the Ability to Block the Interaction of GAL9 with TIM-3

Wells of a Maxisorp 96 well plate were coated with recombinant human Galectin-9 (R&D; cat. no. 2045-GA) at 5 µg/ml in PBS and incubated overnight at 4° C. Wells were washed three times with PBS, and subsequently blocked with 3% BSA in PBS (block buffer) for one hour at room temperature. Thereafter, wells were incubated for one hour at room temperature with 0.1875 µg/ml huTIM-3 Fc (R&D; cat. no. 2365-TM) diluted in block buffer in the presence or absence of 25 µg/ml IgG. Wells were washed three times with PBST (0.05% v/v Tween20 in PBS), and incubated for one hour with biotin conjugated anti-human Fc antibody (Invitrogen; cat. no. AH1309) diluted 1:2000 in block buffer. Next, wash steps were repeated and wells were incubated with HRP-conjugated streptavidin (Becton Dickinson: cat. no. 554066) diluted 1:2000 in blockbuffer for 15 minutes at room temperature. For detection of bound streptavidin, wells were washed three times with PBST and incubated with TMB substrate components A and B (1:1 ratio) (Becton Dickinson; cat. no. 51-2606KC and 51-2607KC, respectively). Reaction was stopped after 10 minutes with 1M $H_2SO_4$ and the OD450 was measured using an ELISA plate reader. ELISA signals lower than 95% of control are considered to represent blocking activity (Table 2).

Affinity Ranking huTIM-3 and huPD-1 Specific Fab Arms Present in the TIM-3×TT and PD-1×TT Bispecific IgG Bispecific antibodies that were shown to bind the respective human and macaque orthologs in FACS were ranked on apparent affinity for both orthologs in FACS. Therefore, the stable cell lines expressing the respective orthologs (Table 1) were harvested and diluted to $10^6$ cells/ml in FACS buffer (PBS/0.5% BSA/0.5 mM EDTA). Cells were centrifuged for 2 minutes at 300 g at 4° C. Supernatant was discarded by inverting the plate(s). 50 µl of each IgG sample, in a 11-step. 2-fold dilution series ranging from 10 to 0.01 µg/ml, was added and incubated for 1H on ice. Cells were centrifuged once, supernatant was removed and cells were washed twice with 150 µl of FACS buffer. 50 µl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a ITS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

Reference Antibodies

Antibodies that inhibit the function of PD-1 are known in the art. Monoclonal bivalent antibodies were constructed according to published information and expressed in CHO-S cells. The anti-PD-1 antibody Nivolumab was generated based on the information disclosed in CA 02607147.

PD-1/PD-L1 Blockade Reporter Assay

The PD-1/PD-L1 blockade reporter assays used were developed by Promega and are based on a two cell system; CHK) cells expressing PD-L1, and a T cell activator and a Jurkat/NFAT-RE Reporter Cell Line overexpressing PD-1. The PD-1/PD-L1 blockade reporter assays were performed using the thaw and use format of Promega. PD-L1 expressing cells (cat. no. C187103) were thawed in 14.5 ml Cell Recovery Medium (DMEM/F12 containing 10% FBS). Next, 50 µl cell suspension was added to the inner wells of a 96 well half area plate (Corning, cat. no. 3688). Plates were incubated overnight at 37° C., 5% CO, in 95% relative humidity. Next day, culture medium was removed and 20 µl test antibody in assay medium (RPMI 1640 containing 4% FBS) in a serial dilution (starting concentration 10 □g/ml) was added to each well. Each plate contained a serial dilution of negative (Ctrl Ab) and positive control antibody (Nivolumab) that served as reference controls. PD-1 effector cells (cat no. C187105) were thawed in 5.9 ml Assay medium and 20 µl cell suspension was added to each well.

Plates were incubated for 6 H or overnight at 37° C. 5% CO, in 95% relative humidity. 40 µl of luciferase (Bio-Glo Luciferase Assay System, cat. no. G1794L) was added the next day and the amount of luciferase activity was measured using aBioTek Synergy 2 Multi-Mode Microplate Reader. Potency was measured as luciferase activity in comparison to the negative control antibody.

Screening of the PD-1 Antibody Panel

VH from the PD-1 antibody panel were produced in 24 well format and tested as bivalent antibodies in a semi log serial titration (starting concentration 10 µg/ml) in the PD-1/PD-L1 blockade reporter assay to rank the antibodies for blocking potency in comparison to Nivolumab. Based on the activity data antibodies were selected from the PD-1 antibody panel for the subsequent PD1×LAG-3 bispecific screen. The activity of the selected candidates in the reporter assay is shown in Table 3. The PD-1 Fab panel was composed of functional activity variants within two antibody, clusters i.e. A and B.

Galectin-9 blocking Fab arms are combined with PD-1 Fab arms and tested for their capacity to restore functionality of exhausted antigen specific T cells.

Example 4

Bispecific PD-1×TIM-3 Antibodies Enhance IFNγ Production by CD4+ T Cells in a Mixed Lymphocyte Reaction.

Mixed lymphocyte reaction (MLR) assays are commonly used to understand the effects of antibodies on T-cell activation and proliferation. Such assays aid understanding of whether such compounds will affect the potential of T cells to mount a response in the tumor microenvironment. Here we used an allogeneic MLR protocol with immature DCs to determine the ability of bispecific PD-1×TIM-3 antibodies to enhance IFNγ production by CD4+ T cells, compared with that of benchmark reference antibodies. The responsiveness of the T cells was quantified by measuring the levels of IFNγ in culture supernatant.

To this end, human peripheral blood mononuclear cells (PBMCs) from healthy donors were prepared from buffy coats. Immature monocyte-derived dendritic cells (Mo-DCs) were prepared by isolating CD14+ cells (EasySep Stemcell, lot no. 16C69672) using magnetic activated cell sorting (MACS) and culturing these in differentiation medium for seven days. Responder T cells derived from a different donor to that used for the Mo-DCs were prepared from cryopreserved PBMCs on the day required, using a T-cell isolation kit (EasySep Stemcell, lot no. 16D70573) to obtain untouched T cells. Six separate MLRs were performed to provide biological replication.

For the assay, $1 \times 10^4$ immature Mo-DCs were co-cultured with $1 \times 10^5$ CD4+ T cells for 4 days, in the presence or absence of test antibody at an end concentration of 10 µg/mL. Cultures were performed in triplicate. Supernatants were collected at the end of the culture period and assessed for IFNγ by ELISA (R&D BioTechne, lot no. 342687) according to the manufacturer's instructions with plates read at 450 nm.

Results

The MLR study comprised experimental groups of a Tim3/PD1 bispecific (PB16465=MF7677×MF6930) and 3 Isotype control group (mono-specific antibodies against a TIM-3 surrogate antibody. Tetanus and mIgG1). Single cell controls and a vehicle control group were also included.

Cultures were performed in triplicate to provide technical replicates. At the end of the 4-day culture period supernatant was collected and ELISAs performed to assess effects of the antibodies on the production of IFN-γ, according to manufacturer's instructions with plates read at 450 nM.

CD14+ cells were sorted on D0 and cultured for 7 days, immature DCs were used on D7 and mature DCs were obtained by culturing for an additional 3 days in maturation medium. CD14 positivity was assessed at D0 to confirm purity of the initial sort, and in immature and matured DCs at D7 and D10, respectively, to confirm downregulation of CD14 to indicate differentiation to Mo-DCs (data not shown). Viability and activation markers (CD80. CD83 and CD86) were also assessed on both immature and matured DCs to confirm differentiation and maturation. Mo-DCs (immature or mature) were cultured with responder T cells for 4 days before supernatant was collected and ELISAs performed to assess effects of the test, antibodies on production of IFN-γ.

In FIG. 11 the results of the test are shown. The bispecific antibody specific for PD-1/TIM-3 out-performed IFN-γ production by CD14+ T cells in MLR over the control and Tim3 surrogate monospecific antibody.

TABLE 1

Expression constructs for each target that were used for DNA immunization (pVAX1 vector based) and for generation of stable Freestyle 293F or CHO-S cell lines (pIRES-neo3 vector based or similar)

| Target | Vectors | Stable cell line |
| --- | --- | --- |
| PD-1 | pVAX1_huPD-1 | NA |
|  | pIRES-neo3_huPD-1 | CHO-S_huPD-1 |
|  | pIRES-neo3_maPD-1 | CHO-S_maPD-1 |
| TIM-3 | pVAX_huTIM-3 | NA |
|  | pIRES-neo3_huTIM-3 | Freestyle 293F_huTIM-3 |
|  | pIRES-neo3_maTIM-3 | Freestyle 293F_maTIM-3 | hu = human,
ma = macaque,
NA = not applicable

TABLE 2

| PB# | first Fab arm | second Fab arm | control | OD |
| --- | --- | --- | --- | --- |
| PB16464 | MF6930 | MF7676 |  | 1.198 |
| PB16465 | MF6930 | MF7677 |  | 0.764 |
| PB16466 | MF6930 | MF7678 |  | 0.872 |
| PB16467 | MF6930 | MF7679 |  | 1.187 |
|  |  |  | ctrl mAb | 1.151 |

Galectin-9 blocking activity of TIM-3×PD-1 bispecific antibodies as determined by ELISA in comparison to a negative control antibody (Ctrl mAb). PB and composition of Fab arms are indicated.

TABLE 3

Functional activity of PD-1 Fab arms as measured in the PD-1/PD-L1 blockade reporter assay as a bivalent antibody in comparison to the positive control Nivolumab. Variants of the same cluster (B) that displayed different PD-1 blocking activity were tested.

| Clone | CDR3 | Cluster | % Activity of pos control |
| --- | --- | --- | --- |
| MF6226 | GGYSGYGGDSFDL (SEQ ID NO: 21) | A | 47.77614647 |
| MF6256 | GTVEATLLFDF (SEQ ID NO: 22) | B | 57.85260834 |
| MF6930 | GTVEATLLFDY (SEQ ID NO: 23) | B | 51.50445453 |

The invention claimed is:

1. An antibody or variant thereof that comprises a variable domain that can bind to an extracellular part of PD-1 and a variable domain that can bind to an extracellular part of TIM-3;
wherein said variable domain that can bind to an extracellular part of PD-1 comprises a heavy chain variable region with a CDR1, CDR2 and CDR3 region that comprises the amino acid sequence of the CDR1, CDR2 and CDR3 of a heavy chain variable region of any one of the VH according to SEQ ID NOs: 43-53 and
a light chain variable region comprising the CDR1 sequence QSISSY (SEQ ID NO:59), the CDR2 sequence AAS, and the CDR3 sequence QQSYSTPPT (SEQ ID NO:60); and
wherein said variable domain that can bind to an extracellular part of TIM-3 comprises a heavy chain variable region with a CDR1, CDR2 and CDR3 region that comprises the amino acid sequence of the CDR1, CDR2 and CDR3 of a heavy chain variable region of any one of the VH according to SEQ ID NOs:54-57, and a light chain variable region comprising the CDR1 sequence QSISSY (SEQ ID NO:59), the CDR2 sequence AAS, and the CDR3 sequence QQSYSTPPT (SEQ ID NO:60).

2. The antibody or variant thereof of claim 1, wherein the variable domain that binds PD-1 blocks the binding of PD-1 to PD-L1 and/or PD-L2.

3. The antibody of claim 1, wherein the variable domain that binds TIM-3, blocks the binding of TIM-3 to Galectin-9.

4. The antibody or variant thereof of claim 1, wherein the variable domain that binds an extracellular part of PD-1 is defined as a variable region that when in a bivalent monospecific antibody that comprises two of said variable domains that bind PD-1, inhibits PD-1/PD-L1 inhibition in a Jurkat cell in a range of 20-150% when compared to the inhibition obtained with the antibody Nivolumab on a Jurkat cell.

5. The antibody or variant thereof of claim 1, wherein the variable domain that can bind to an extra cellular part of PD-1 comprises a heavy chain variable region that comprises the amino acid sequence of the variable heavy chain region of any one of SEQ ID NOs:43-53, having at most 15 conservative amino acid substitutions, wherein said substitutions are not in the CDR1, CDR2 or CDR3 of the variable heavy chain region.

6. The antibody or variant thereof of claim 1, wherein the variable domain that can bind to an extra cellular part of TIM-3 comprises a heavy chain variable region that comprises the amino acid sequence of the heavy chain variable region according to any one of SEQ ID NOs:54-57, having at most 15 conservative amino acid substitutions, wherein said substitutions are not in the CDR1, CDR2 or CDR3 of said heavy chain variable region.

7. The antibody or variant thereof of claim 1, wherein the antibody comprises:
   a variable domain that can bind to an extracellular part of TIM-3 which comprises a heavy chain variable region that comprises the amino acid sequence of the heavy chain variable region according to any one of SEQ ID NOs:54-57, having at most 15 conservative amino acid substitutions, wherein said substitutions are not in the CDR1, CDR2 or CDR3 of said heavy chain variable region, and
   a variable domain that can bind to an extracellular part of PD-1 which comprises a heavy chain variable region that comprises the amino acid sequence of the heavy chain variable region according to SEQ ID NO: 47, having at most 15 conservative amino acid substitutions, wherein said substitutions are not in the CDR1, CDR2 or CDR3 of said heavy chain variable region.

8. The antibody or variant thereof of claim 1, which comprises a light chain variable region having a sequence that is at least 90% identical to the amino acid sequence according to SEQ ID NO:26, comprising the CDR1 sequence QSISSY (SEQ ID NO:59), the CDR2 sequence AAS, and the CDR3 sequence QQSYSTPPT (SEQ ID NO:60).

9. A composition or kit of parts comprising at least one antibody or variant thereof according to claim 1.

10. A pharmaceutical composition comprising at least one antibody or variant thereof of claim 1 and a pharmaceutically acceptable carrier, diluent or excipient.

11. The antibody or variant thereof of claim 1, wherein the variable domain that can bind to an extracellular part of PD-1 comprises a heavy chain variable region with a CDR1, CDR2 and CDR3 region that comprises the amino acid sequence of the CDR1, CDR2 and CDR3 of a heavy chain variable region of any one of the VH according to SEQ ID NOs: 43, 46, 47 or 52.

12. The antibody or variant thereof of claim 1, wherein the antibody comprises:
   a variable domain that can bind to an extracellular part of TIM-3 which comprises a heavy chain variable region that comprises the amino acid sequence of the heavy chain variable region according to any one of SEQ ID NOs: 54-57, having at most 15 conservative amino acid substitutions, wherein said substitutions are not in the CDR1, CDR2 or CDR3 of said heavy chain variable region; and
   a variable domain that can bind to an extracellular part of PD-1 which comprises a heavy chain variable region that comprises the amino acid sequence of the heavy chain variable region according to SEQ ID NO: 43, having at most 15 conservative amino acid substitutions, wherein said substitutions are not in the CDR1, CDR2 or CDR3 of said heavy chain variable region.

13. The antibody or variant thereof of claim 1, wherein the antibody comprises:
   a variable domain that can bind to an extracellular part of TIM-3 which comprises a heavy chain variable region that comprises the amino acid sequence of the heavy chain variable region according to any one of SEQ ID NOs: 54-57, having at most 15 conservative amino acid substitutions, wherein said substitutions are not in the CDR1, CDR2 or CDR3 of said heavy chain variable region; and
   a variable domain that can bind to an extracellular part of PD-1 which comprises a heavy chain variable region that comprises the amino acid sequence of the heavy chain variable region according to SEQ ID NO: 46, having at most 15 conservative amino acid substitutions, wherein said substitutions are not in the CDR1, CDR2 or CDR3 of said heavy chain variable region.

14. The antibody or variant thereof of claim 1, wherein the antibody comprises:
   a variable domain that can bind to an extracellular part of TIM-3 which comprises a heavy chain variable region that comprises the amino acid sequence of the heavy chain variable region according to any one of SEQ ID NOs: 54-57, having at most 15 conservative amino acid substitutions, wherein said substitutions are not in the CDR1, CDR2 or CDR3 of said heavy chain variable region; and
   a variable domain that can bind to an extracellular part of PD-1 which comprises a heavy chain variable region that comprises the amino acid sequence of the heavy chain variable region according to SEQ ID NO: 52, having at most 15 conservative amino acid substitutions, wherein said substitutions are not in the CDR1, CDR2 or CDR3 of said heavy chain variable region.

\* \* \* \* \*

SEQUENCE LISTING

<160> NUMBER OF SEQ ID NOS: 60

<210> SEQ ID NO 1
<211> LENGTH: 288
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: DOMAIN
<222> LOCATION: (21)..(170)
<223> OTHER INFORMATION: ECD
<220> FEATURE:
<221> NAME/KEY: DOMAIN
<222> LOCATION: (171)..(191)
<223> OTHER INFORMATION: TM
<220> FEATURE:
<221> NAME/KEY: DOMAIN
<222> LOCATION: (192)..(288)
<223> OTHER INFORMATION: Intracellular tail

<400> SEQUENCE: 1

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 2
<211> LENGTH: 20
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg
            20

<210> SEQ ID NO 3
<211> LENGTH: 150
<212> TYPE: PRT
<213> ORGANISM: Homo sapiens

<400> SEQUENCE: 3

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 4
<211> LENGTH: 21
<212> TYPE: PRT
<213> ORGANISM: Homo sapiens

<400> SEQUENCE: 4

Val Gly Val Val Gly Gly Leu Leu Gly Ser Leu Val Leu Leu Val Trp
1               5                   10                  15

Val Leu Ala Val Ile
            20

<210> SEQ ID NO 5
<211> LENGTH: 97
<212> TYPE: PRT
<213> ORGANISM: Homo sapiens

<400> SEQUENCE: 5

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
                20                  25                  30

```
Gly Glu Leu Asp Phe Gln Trp Arg Glu Lys Thr Pro Glu Pro Pro Val
         35                  40                  45

Pro Cys Val Pro Glu Gln Thr Glu Tyr Ala Thr Ile Val Phe Pro Ser
 50                  55                  60

Gly Met Gly Thr Ser Ser Pro Ala Arg Arg Gly Ser Ala Asp Gly Pro
 65                  70                  75                  80

Arg Ser Ala Gln Pro Leu Arg Pro Glu Asp Gly His Cys Ser Trp Pro
             85                  90                  95

Leu

<210> SEQ ID NO 6
<211> LENGTH: 288
<212> TYPE: PRT
<213> ORGANISM: Macaca fascicularis
<220> FEATURE:
<221> NAME/KEY: SIGNAL
<222> LOCATION: (1)..(20)
<220> FEATURE:
<221> NAME/KEY: DOMAIN
<222> LOCATION: (21)..(170)
<223> OTHER INFORMATION: ECD
<220> FEATURE:
<221> NAME/KEY: DOMAIN
<222> LOCATION: (171)..(191)
<223> OTHER INFORMATION: TM
<220> FEATURE:
<221> NAME/KEY: DOMAIN
<222> LOCATION: (192)..(288)
<223> OTHER INFORMATION: Intracellular tail

<400> SEQUENCE: 6

Met Gln Ile Pro Gln Ala Pro Trp Pro Val Val Trp Ala Val Leu Gln
 1               5                  10                  15

Leu Gly Trp Arg Pro Gly Trp Phe Leu Glu Ser Pro Asp Arg Pro Trp
             20                  25                  30

Asn Ala Pro Thr Phe Ser Pro Ala Leu Leu Val Thr Glu Gly Asp
         35                  40                  45

Asn Ala Thr Phe Thr Cys Ser Phe Ser Asn Ala Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
             85                  90                  95

Val Thr Arg Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
            165                 170                 175

Leu Leu Gly Ser Leu Val Leu Leu Val Trp Val Leu Ala Val Ile Cys
        180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
        210                 215                 220
```

```
Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285
```

<210> SEQ ID NO 7
<211> LENGTH: 20
<212> TYPE: PRT
<213> ORGANISM: Macaca fascicularis

<400> SEQUENCE: 7

```
Met Gln Ile Pro Gln Ala Pro Trp Pro Val Val Trp Ala Val Leu Gln
1               5                   10                  15

Leu Gly Trp Arg
            20
```

<210> SEQ ID NO 8
<211> LENGTH: 150
<212> TYPE: PRT
<213> ORGANISM: Macaca fascicularis

<400> SEQUENCE: 8

```
Pro Gly Trp Phe Leu Glu Ser Pro Asp Arg Pro Trp Asn Ala Pro Thr
1               5                   10                  15

Phe Ser Pro Ala Leu Leu Leu Val Thr Glu Gly Asp Asn Ala Thr Phe
                20                  25                  30

Thr Cys Ser Phe Ser Asn Ala Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Arg Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Ala Leu Val
145                 150
```

<210> SEQ ID NO 9
<211> LENGTH: 21
<212> TYPE: PRT
<213> ORGANISM: Macaca fascicularis

<400> SEQUENCE: 9

```
Val Gly Val Val Gly Gly Leu Leu Gly Ser Leu Val Leu Leu Val Trp
1               5                   10                  15

Val Leu Ala Val Ile
            20
```

-continued

<210> SEQ ID NO 10
<211> LENGTH: 97
<212> TYPE: PRT
<213> ORGANISM: Macaca fascicularis

<400> SEQUENCE: 10

Cys Ser Arg Ala Ala Gln Gly Thr Ile Glu Ala Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Ala
        35                  40                  45

Pro Cys Val Pro Glu Gln Thr Glu Tyr Ala Thr Ile Val Phe Pro Ser
    50                  55                  60

Gly Leu Gly Thr Ser Ser Pro Ala Arg Arg Gly Ser Ala Asp Gly Pro
65                  70                  75                  80

Arg Ser Pro Arg Pro Leu Arg Pro Glu Asp Gly His Cys Ser Trp Pro
                85                  90                  95

Leu

<210> SEQ ID NO 11
<211> LENGTH: 301
<212> TYPE: PRT
<213> ORGANISM: Homo sapiens
<220> FEATURE:
<221> NAME/KEY: SIGNAL
<222> LOCATION: (1)..(21)
<220> FEATURE:
<221> NAME/KEY: DOMAIN
<222> LOCATION: (22)..(202)
<223> OTHER INFORMATION: ECD
<220> FEATURE:
<221> NAME/KEY: DOMAIN
<222> LOCATION: (203)..(223)
<223> OTHER INFORMATION: TM
<220> FEATURE:
<221> NAME/KEY: DOMAIN
<222> LOCATION: (224)..(301)
<223> OTHER INFORMATION: Intracellular tail

<400> SEQUENCE: 11

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala

```
                    145                 150                 155                 160
Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300
```

<210> SEQ ID NO 12
<211> LENGTH: 21
<212> TYPE: PRT
<213> ORGANISM: Homo sapiens

<400> SEQUENCE: 12

```
Met Phe Ser His Leu Pro Phe Asp Cys Val Leu Leu Leu Leu Leu Leu
1               5                   10                  15

Leu Leu Thr Arg Ser
            20
```

<210> SEQ ID NO 13
<211> LENGTH: 181
<212> TYPE: PRT
<213> ORGANISM: Homo sapiens

<400> SEQUENCE: 13

```
Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Leu Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
```

```
                145                 150                 155                 160
Glu Leu Arg Asp Ser Arg Leu Ala Asn Asp Leu Arg Asp Ser Gly Ala
                165                 170                 175
Thr Ile Arg Ile Gly
            180

<210> SEQ ID NO 14
<211> LENGTH: 21
<212> TYPE: PRT
<213> ORGANISM: Homo sapiens

<400> SEQUENCE: 14

Ile Tyr Ile Gly Ala Gly Ile Cys Ala Gly Leu Ala Leu Ala Leu Ile
1               5                   10                  15

Phe Gly Ala Leu Ile
            20

<210> SEQ ID NO 15
<211> LENGTH: 78
<212> TYPE: PRT
<213> ORGANISM: Homo sapiens

<400> SEQUENCE: 15

Phe Lys Trp Tyr Ser His Ser Lys Glu Lys Ile Gln Asn Leu Ser Leu
1               5                   10                  15

Ile Ser Leu Ala Asn Leu Pro Pro Ser Gly Leu Ala Asn Ala Val Ala
                20                  25                  30

Glu Gly Ile Arg Ser Glu Glu Asn Ile Tyr Thr Ile Glu Glu Asn Val
            35                  40                  45

Tyr Glu Val Glu Glu Pro Asn Glu Tyr Tyr Cys Tyr Val Ser Ser Arg
        50                  55                  60

Gln Gln Pro Ser Gln Pro Leu Gly Cys Arg Phe Ala Met Pro
65                  70                  75

<210> SEQ ID NO 16
<211> LENGTH: 301
<212> TYPE: PRT
<213> ORGANISM: Macaca fascicularis
<220> FEATURE:
<221> NAME/KEY: SIGNAL
<222> LOCATION: (1)..(21)
<220> FEATURE:
<221> NAME/KEY: DOMAIN
<222> LOCATION: (22)..(202)
<223> OTHER INFORMATION: ECD
<220> FEATURE:
<221> NAME/KEY: DOMAIN
<222> LOCATION: (203)..(223)
<223> OTHER INFORMATION: TM
<220> FEATURE:
<221> NAME/KEY: DOMAIN
<222> LOCATION: (224)..(301)
<223> OTHER INFORMATION: Intracellular tail

<400> SEQUENCE: 16

Met Phe Ser His Leu Pro Phe Asp Cys Val Leu Leu Leu Leu Leu Leu
1               5                   10                  15

Leu Leu Thr Arg Ser Ser Glu Val Glu Tyr Ile Ala Glu Val Gly Gln
                20                  25                  30

Asn Ala Tyr Leu Pro Cys Ser Tyr Thr Pro Ala Pro Gly Asn Leu
            35                  40                  45

Val Pro Val Cys Trp Gly Lys Gly Ala Cys Pro Val Phe Asp Cys Ser
        50                  55                  60
```

```
Asn Val Val Leu Arg Thr Asp Asn Arg Asp Val Asn Asp Arg Thr Ser
 65                  70                  75                  80

Gly Arg Tyr Trp Leu Lys Gly Asp Phe His Lys Gly Asp Val Ser Leu
                 85                  90                  95

Thr Ile Glu Asn Val Thr Leu Ala Asp Ser Gly Val Tyr Cys Cys Arg
            100                 105                 110

Ile Gln Ile Pro Gly Ile Met Asp Glu Lys His Asn Val Lys Leu Val
        115                 120                 125

Val Ile Lys Pro Ala Lys Val Thr Pro Ala Pro Thr Leu Gln Arg Asp
    130                 135                 140

Leu Thr Ser Ala Phe Pro Arg Met Leu Thr Thr Gly Glu His Gly Pro
145                 150                 155                 160

Ala Glu Thr Gln Thr Pro Gly Ser Leu Pro Asp Val Asn Leu Thr Val
                165                 170                 175

Ser Asn Phe Phe Cys Glu Leu Gln Ile Phe Thr Leu Thr Asn Glu Leu
            180                 185                 190

Arg Asp Ser Gly Ala Thr Ile Arg Thr Ala Ile Tyr Ile Ala Ala Gly
        195                 200                 205

Ile Ser Ala Gly Leu Ala Leu Ala Leu Ile Phe Gly Ala Leu Ile Phe
    210                 215                 220

Lys Trp Tyr Ser His Ser Lys Glu Lys Thr Gln Asn Leu Ser Leu Ile
225                 230                 235                 240

Ser Leu Ala Asn Ile Pro Pro Ser Gly Leu Ala Asn Ala Val Ala Glu
                245                 250                 255

Gly Ile Arg Ser Glu Glu Asn Ile Tyr Thr Ile Glu Glu Asp Val Tyr
            260                 265                 270

Glu Val Glu Glu Pro Asn Glu Tyr Tyr Cys Tyr Val Ser Ser Gly Gln
        275                 280                 285

Gln Pro Ser Gln Pro Leu Gly Cys Arg Val Ala Met Pro
    290                 295                 300

<210> SEQ ID NO 17
<211> LENGTH: 21
<212> TYPE: PRT
<213> ORGANISM: Macaca fascicularis

<400> SEQUENCE: 17

Met Phe Ser His Leu Pro Phe Asp Cys Val Leu Leu Leu Leu Leu Leu
1               5                   10                  15

Leu Leu Thr Arg Ser
            20

<210> SEQ ID NO 18
<211> LENGTH: 181
<212> TYPE: PRT
<213> ORGANISM: Macaca fascicularis

<400> SEQUENCE: 18

Ser Glu Val Glu Tyr Ile Ala Glu Val Gly Gln Asn Ala Tyr Leu Pro
1               5                   10                  15

Cys Ser Tyr Thr Pro Ala Pro Pro Gly Asn Leu Val Pro Val Cys Trp
                20                  25                  30

Gly Lys Gly Ala Cys Pro Val Phe Asp Cys Ser Asn Val Val Leu Arg
            35                  40                  45

Thr Asp Asn Arg Asp Val Asn Asp Arg Thr Ser Gly Arg Tyr Trp Leu
        50                  55                  60
```

```
Lys Gly Asp Phe His Lys Gly Asp Val Ser Leu Thr Ile Glu Asn Val
 65                  70                  75                  80

Thr Leu Ala Asp Ser Gly Val Tyr Cys Cys Arg Ile Gln Ile Pro Gly
                 85                  90                  95

Ile Met Asp Glu Lys His Asn Val Lys Leu Val Val Ile Lys Pro Ala
            100                 105                 110

Lys Val Thr Pro Ala Pro Thr Leu Gln Arg Asp Leu Thr Ser Ala Phe
        115                 120                 125

Pro Arg Met Leu Thr Thr Gly Glu His Gly Pro Ala Glu Thr Gln Thr
    130                 135                 140

Pro Gly Ser Leu Pro Asp Val Asn Leu Thr Val Ser Asn Phe Phe Cys
145                 150                 155                 160

Glu Leu Gln Ile Phe Thr Leu Thr Asn Glu Leu Arg Asp Ser Gly Ala
                165                 170                 175

Thr Ile Arg Thr Ala
            180

<210> SEQ ID NO 19
<211> LENGTH: 21
<212> TYPE: PRT
<213> ORGANISM: Macaca fascicularis

<400> SEQUENCE: 19

Ile Tyr Ile Ala Ala Gly Ile Ser Ala Gly Leu Ala Leu Ala Leu Ile
1               5                   10                  15

Phe Gly Ala Leu Ile
            20

<210> SEQ ID NO 20
<211> LENGTH: 78
<212> TYPE: PRT
<213> ORGANISM: Macaca fascicularis

<400> SEQUENCE: 20

Phe Lys Trp Tyr Ser His Ser Lys Glu Lys Thr Gln Asn Leu Ser Leu
1               5                   10                  15

Ile Ser Leu Ala Asn Ile Pro Pro Ser Gly Leu Ala Asn Ala Val Ala
            20                  25                  30

Glu Gly Ile Arg Ser Glu Glu Asn Ile Tyr Thr Ile Glu Glu Asp Val
        35                  40                  45

Tyr Glu Val Glu Glu Pro Asn Glu Tyr Tyr Cys Tyr Val Ser Ser Gly
    50                  55                  60

Gln Gln Pro Ser Gln Pro Leu Gly Cys Arg Val Ala Met Pro
65                  70                  75

<210> SEQ ID NO 21
<211> LENGTH: 13
<212> TYPE: PRT
<213> ORGANISM: Artificial Sequence
<220> FEATURE:
<223> OTHER INFORMATION: CDR3 of MF6226

<400> SEQUENCE: 21

Gly Gly Tyr Ser Gly Tyr Gly Gly Asp Ser Phe Asp Leu
1               5                   10

<210> SEQ ID NO 22
<211> LENGTH: 11
<212> TYPE: PRT
```

```
<213> ORGANISM: Artificial Sequence
<220> FEATURE:
<223> OTHER INFORMATION: CDR3 of MF6256

<400> SEQUENCE: 22

Gly Thr Val Glu Ala Thr Leu Leu Phe Asp Phe
1               5                   10

<210> SEQ ID NO 23
<211> LENGTH: 11
<212> TYPE: PRT
<213> ORGANISM: Artificial Sequence
<220> FEATURE:
<223> OTHER INFORMATION: CDR3 of MF6930

<400> SEQUENCE: 23

Gly Thr Val Glu Ala Thr Leu Leu Phe Asp Tyr
1               5                   10

<210> SEQ ID NO 24
<211> LENGTH: 214
<212> TYPE: PRT
<213> ORGANISM: Artificial Sequence
<220> FEATURE:
<223> OTHER INFORMATION: Common light chain used in mono- and bispecific
    IgG

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 321
<212> TYPE: DNA
```

```
<213> ORGANISM: Artificial Sequence
<220> FEATURE:
<223> OTHER INFORMATION: Common light chain variable domain
<220> FEATURE:
<221> NAME/KEY: CDS
<222> LOCATION: (1)..(321)

<400> SEQUENCE: 25 gac atc cag atg acc cag tct cca tcc tcc ctg tct gca tct gta gga        48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac        96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc       144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc       192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct       240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca       288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                           321
Thr Phe Gly Gln Gly Thr Lys Val Glu Ile Lys
                100                 105

<210> SEQ ID NO 26
<211> LENGTH: 107
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
                100                 105

<210> SEQ ID NO 27
<211> LENGTH: 324
<212> TYPE: DNA
<213> ORGANISM: Artificial Sequence
<220> FEATURE:
<223> OTHER INFORMATION: Common light chain constant region
<220> FEATURE:
<221> NAME/KEY: CDS
<222> LOCATION: (1)..(324)
```

-continued

```
<400> SEQUENCE: 27 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105

<210> SEQ ID NO 28
<211> LENGTH: 107
<212> TYPE: PRT
<213> ORGANISM: Artificial Sequence
<220> FEATURE:
<223> OTHER INFORMATION: Synthetic Construct

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 108
<212> TYPE: PRT
<213> ORGANISM: Artificial Sequence
<220> FEATURE:
<223> OTHER INFORMATION: IGKV1-39/jk5 common light chain variable domain

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
                100                 105

<210> SEQ ID NO 30
<211> LENGTH: 95
<212> TYPE: PRT
<213> ORGANISM: Artificial Sequence
<220> FEATURE:
<223> OTHER INFORMATION: V-region IGKV1-39A

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95

<210> SEQ ID NO 31
<211> LENGTH: 294
<212> TYPE: DNA
<213> ORGANISM: Artificial Sequence
<220> FEATURE:
<223> OTHER INFORMATION: CH1 region
<220> FEATURE:
<221> NAME/KEY: CDS
<222> LOCATION: (1)..(294)

<400> SEQUENCE: 31 gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
 1               5                  10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
                20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
             35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
         50                  55                  60 ctc agc agc gtc gtg acc gtg ccc tcc agc agc ttg ggc acc cag acc     240
Leu Ser Ser Val Val Thr Val Pro Ser Ser Ser Leu Gly Thr Gln Thr
 65                  70                  75                  80 tac atc tgc aac gta aat cac aag ccc agc aac acc aag gtg gac aag     288
Tyr Ile Cys Asn Val Asn His Lys Pro Ser Asn Thr Lys Val Asp Lys
                 85                  90                  95 aga gtt                                                             294
```

Arg Val

<210> SEQ ID NO 32
<211> LENGTH: 98
<212> TYPE: PRT
<213> ORGANISM: Artificial Sequence
<220> FEATURE:
<223> OTHER INFORMATION: Synthetic Construct

<400> SEQUENCE: 32

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val
```

<210> SEQ ID NO 33
<211> LENGTH: 45
<212> TYPE: DNA
<213> ORGANISM: Artificial Sequence
<220> FEATURE:
<223> OTHER INFORMATION: hinge region
<220> FEATURE:
<221> NAME/KEY: CDS
<222> LOCATION: (1)..(45)

<400> SEQUENCE: 33

```
gag ccc aaa tct tgt gac aaa act cac aca tgc cca ccg tgc cca          45
Glu Pro Lys Ser Cys Asp Lys Thr His Thr Cys Pro Pro Cys Pro
1               5                   10                  15
```

<210> SEQ ID NO 34
<211> LENGTH: 15
<212> TYPE: PRT
<213> ORGANISM: Artificial Sequence
<220> FEATURE:
<223> OTHER INFORMATION: Synthetic Construct

<400> SEQUENCE: 34

```
Glu Pro Lys Ser Cys Asp Lys Thr His Thr Cys Pro Pro Cys Pro
1               5                   10                  15
```

<210> SEQ ID NO 35
<211> LENGTH: 330
<212> TYPE: DNA
<213> ORGANISM: Artificial Sequence
<220> FEATURE:
<223> OTHER INFORMATION: CH2 region
<220> FEATURE:
<221> NAME/KEY: CDS
<222> LOCATION: (1)..(330)

<400> SEQUENCE: 35

```
gca cct gaa ctc ctg ggg gga ccg tca gtc ttc ctc ttc ccc cca aaa      48
Ala Pro Glu Leu Leu Gly Gly Pro Ser Val Phe Leu Phe Pro Pro Lys
1               5                   10                  15
```

| | | |
|---|---|---|
| ccc aag gac acc ctc atg atc tcc cgg acc cct gag gtc aca tgc gtg<br>Pro Lys Asp Thr Leu Met Ile Ser Arg Thr Pro Glu Val Thr Cys Val<br>20 25 30 | | 96 |
| gtg gtg gac gtg agc cac gaa gac cct gag gtc aag ttc aac tgg tac<br>Val Val Asp Val Ser His Glu Asp Pro Glu Val Lys Phe Asn Trp Tyr<br>35 40 45 | | 144 |
| gtg gac ggc gtg gag gtg cat aat gcc aag aca aag ccg cgg gag gag<br>Val Asp Gly Val Glu Val His Asn Ala Lys Thr Lys Pro Arg Glu Glu<br>50 55 60 | | 192 |
| cag tac aac agc acg tac cgt gtg gtc agc gtc ctc acc gtc ctg cac<br>Gln Tyr Asn Ser Thr Tyr Arg Val Val Ser Val Leu Thr Val Leu His<br>65 70 75 80 | | 240 |
| cag gac tgg ctg aat ggc aag gag tac aag tgc aag gtc tcc aac aaa<br>Gln Asp Trp Leu Asn Gly Lys Glu Tyr Lys Cys Lys Val Ser Asn Lys<br>85 90 95 | | 288 |
| gcc ctc cca gcc ccc atc gag aaa acc atc tcc aaa gcc aaa<br>Ala Leu Pro Ala Pro Ile Glu Lys Thr Ile Ser Lys Ala Lys<br>100 105 110 | | 330 |

<210> SEQ ID NO 36
<211> LENGTH: 110
<212> TYPE: PRT
<213> ORGANISM: Artificial Sequence
<220> FEATURE:
<223> OTHER INFORMATION: Synthetic Construct

<400> SEQUENCE: 36

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 37
<211> LENGTH: 330
<212> TYPE: DNA
<213> ORGANISM: Artificial Sequence
<220> FEATURE:
<223> OTHER INFORMATION: CH2 region containing L235G and G236R silencing
      substitutions
<220> FEATURE:
<221> NAME/KEY: CDS
<222> LOCATION: (1)..(330)

<400> SEQUENCE: 37

| | | |
|---|---|---|
| gca cct gaa ctc ggc agg gga ccg tca gtc ttc ctc ttc ccc cca aaa<br>Ala Pro Glu Leu Gly Arg Gly Pro Ser Val Phe Leu Phe Pro Pro Lys<br>1 5 10 15 | | 48 |
| ccc aag gac acc ctc atg atc tcc cgg acc cct gag gtc aca tgc gtg<br>Pro Lys Asp Thr Leu Met Ile Ser Arg Thr Pro Glu Val Thr Cys Val<br>20 25 30 | | 96 |
| gtg gtg gac gtg agc cac gaa gac cct gag gtc aag ttc aac tgg tac<br>Val Val Asp Val Ser His Glu Asp Pro Glu Val Lys Phe Asn Trp Tyr<br>35 40 45 | | 144 |

```
                35                  40                  45
gtg gac ggc gtg gag gtg cat aat gcc aag aca aag ccg cgg gag gag      192
Val Asp Gly Val Glu Val His Asn Ala Lys Thr Lys Pro Arg Glu Glu
         50                  55                  60 cag tac aac agc acg tac cgt gtg gtc agc gtc ctc acc gtc ctg cac      240
Gln Tyr Asn Ser Thr Tyr Arg Val Val Ser Val Leu Thr Val Leu His
 65                  70                  75                  80 cag gac tgg ctg aat ggc aag gag tac aag tgc aag gtc tcc aac aaa      288
Gln Asp Trp Leu Asn Gly Lys Glu Tyr Lys Cys Lys Val Ser Asn Lys
                 85                  90                  95 gcc ctc cca gcc ccc atc gag aaa acc atc tcc aaa gcc aaa              330
Ala Leu Pro Ala Pro Ile Glu Lys Thr Ile Ser Lys Ala Lys
            100                 105                 110

<210> SEQ ID NO 38
<211> LENGTH: 110
<212> TYPE: PRT
<213> ORGANISM: Artificial Sequence
<220> FEATURE:
<223> OTHER INFORMATION: Synthetic Construct

<400> SEQUENCE: 38

Ala Pro Glu Leu Gly Arg Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 39
<211> LENGTH: 321
<212> TYPE: DNA
<213> ORGANISM: Artificial Sequence
<220> FEATURE:
<223> OTHER INFORMATION: CH3 domain containing substitutions L351K and
      T366K (KK)
<220> FEATURE:
<221> NAME/KEY: CDS
<222> LOCATION: (1)..(321)

<400> SEQUENCE: 39 ggg cag ccc cga gaa cca cag gtg tac acc aag ccc cca tcc cgg gag       48
Gly Gln Pro Arg Glu Pro Gln Val Tyr Thr Lys Pro Pro Ser Arg Glu
  1               5                  10                  15 gag atg acc aag aac cag gtc agc ctg aag tgc ctg gtc aaa ggc ttc       96
Glu Met Thr Lys Asn Gln Val Ser Leu Lys Cys Leu Val Lys Gly Phe
                 20                  25                  30 tat ccc agc gac atc gcc gtg gag tgg gag agc aat ggg cag ccg gag      144
Tyr Pro Ser Asp Ile Ala Val Glu Trp Glu Ser Asn Gly Gln Pro Glu
             35                  40                  45 aac aac tac aag acc acg cct ccc gtg ctg gac tcc gac ggc tcc ttc      192
Asn Asn Tyr Lys Thr Thr Pro Pro Val Leu Asp Ser Asp Gly Ser Phe
         50                  55                  60
```

```
ttc ctc tat agc aag ctc acc gtg gac aag agc agg tgg cag cag ggg    240
Phe Leu Tyr Ser Lys Leu Thr Val Asp Lys Ser Arg Trp Gln Gln Gly
 65                  70                  75                  80 aac gtc ttc tca tgc tcc gtg atg cat gag gct ctg cac aac cac tac    288
Asn Val Phe Ser Cys Ser Val Met His Glu Ala Leu His Asn His Tyr
                 85                  90                  95 acg cag aag agc ctc tcc ctg tct ccg ggt tga                        321
Thr Gln Lys Ser Leu Ser Leu Ser Pro Gly
            100                 105

<210> SEQ ID NO 40
<211> LENGTH: 106
<212> TYPE: PRT
<213> ORGANISM: Artificial Sequence
<220> FEATURE:
<223> OTHER INFORMATION: Synthetic Construct

<400> SEQUENCE: 40

Gly Gln Pro Arg Glu Pro Gln Val Tyr Thr Lys Pro Pro Ser Arg Glu
1               5                   10                  15

Glu Met Thr Lys Asn Gln Val Ser Leu Lys Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 41
<211> LENGTH: 321
<212> TYPE: DNA
<213> ORGANISM: Artificial Sequence
<220> FEATURE:
<223> OTHER INFORMATION: CH3 domain containing substitutions L351D and
      L368E (DE)
<220> FEATURE:
<221> NAME/KEY: CDS
<222> LOCATION: (1)..(321)

<400> SEQUENCE: 41 ggg cag ccc cga gaa cca cag gtg tac acc gac ccc cca tcc cgg gag     48
Gly Gln Pro Arg Glu Pro Gln Val Tyr Thr Asp Pro Pro Ser Arg Glu
1               5                   10                  15 gag atg acc aag aac cag gtc agc ctg acc tgc gag gtc aaa ggc ttc     96
Glu Met Thr Lys Asn Gln Val Ser Leu Thr Cys Glu Val Lys Gly Phe
            20                  25                  30 tat ccc agc gac atc gcc gtg gag tgg gag agc aat ggg cag ccg gag    144
Tyr Pro Ser Asp Ile Ala Val Glu Trp Glu Ser Asn Gly Gln Pro Glu
        35                  40                  45 aac aac tac aag acc acg cct ccc gtg ctg gac tcc gac ggc tcc ttc    192
Asn Asn Tyr Lys Thr Thr Pro Pro Val Leu Asp Ser Asp Gly Ser Phe
 50                  55                  60 ttc ctc tat agc aag ctc acc gtg gac aag agc agg tgg cag cag ggg    240
Phe Leu Tyr Ser Lys Leu Thr Val Asp Lys Ser Arg Trp Gln Gln Gly
 65                  70                  75                  80 aac gtc ttc tca tgc tcc gtg atg cat gag gct ctg cac aac cac tac    288
Asn Val Phe Ser Cys Ser Val Met His Glu Ala Leu His Asn His Tyr
```

```
              85                  90                  95
acg cag aag agc ctc tcc ctg tct ccg ggt tga                        321
Thr Gln Lys Ser Leu Ser Leu Ser Pro Gly
            100                 105
```

<210> SEQ ID NO 42
<211> LENGTH: 106
<212> TYPE: PRT
<213> ORGANISM: Artificial Sequence
<220> FEATURE:
<223> OTHER INFORMATION: Synthetic Construct

<400> SEQUENCE: 42

Gly Gln Pro Arg Glu Pro Gln Val Tyr Thr Asp Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 43
<211> LENGTH: 121
<212> TYPE: PRT
<213> ORGANISM: Artificial Sequence
<220> FEATURE:
<223> OTHER INFORMATION: MF6076

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Thr Asp Ser Leu Gly Phe Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Ser Ala Asn Phe Asn Pro Ser Leu Lys
    50                  55                  60

Ser Arg Val Thr Met Ser Ile Asp Thr Ser Asn Asn Gln Phe Ser Leu
65                  70                  75                  80

Lys Leu Arg Ser Val Thr Ala Ala Asp Thr Ala Val Tyr Phe Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser
        115                 120

<210> SEQ ID NO 44
<211> LENGTH: 121
<212> TYPE: PRT
<213> ORGANISM: Artificial Sequence
<220> FEATURE:
<223> OTHER INFORMATION: MF6226

<400> SEQUENCE: 44

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Gly Tyr Tyr
            20                  25                  30

Phe Trp Ser Trp Ile Arg Gln Pro Pro Gly Lys Gly Leu Glu Trp Ile
        35                  40                  45

Gly Tyr Val Tyr Tyr Ser Gly Ser Asn Asn Leu Asn Pro Ser Leu Lys
    50                  55                  60

Ser Arg Val Thr Leu Ser Val Asp Thr Ser Lys Asn Gln Phe Ser Leu
65                  70                  75                  80

Arg Leu Asn Ser Met Thr Ala Ala Asp Thr Ala Val Tyr Tyr Cys Ala
                85                  90                  95

Arg Gly Gly Tyr Ser Gly Tyr Gly Gly Asp Ser Phe Asp Leu Trp Gly
            100                 105                 110

Gln Gly Thr Thr Val Thr Val Ser Ser
        115                 120
```

<210> SEQ ID NO 45
<211> LENGTH: 121
<212> TYPE: PRT
<213> ORGANISM: Artificial Sequence
<220> FEATURE:
<223> OTHER INFORMATION: MF6236

<400> SEQUENCE: 45

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Tyr Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Ser Thr Asn Phe Asn Pro Ser Leu Lys
    50                  55                  60

Ser Arg Val Thr Met Ser Val Asp Thr Ser Lys Asn Gln Phe Ser Leu
65                  70                  75                  80

Asn Leu Arg Ser Val Thr Thr Ala Asp Thr Ala Val Tyr Tyr Cys Ala
                85                  90                  95

Arg Gly Gly Tyr Thr Gly His Gly Gly Asp Trp Phe Asp Pro Trp Gly
            100                 105                 110

Gln Gly Thr Leu Val Thr Val Ser Ser
        115                 120
```

<210> SEQ ID NO 46
<211> LENGTH: 120
<212> TYPE: PRT
<213> ORGANISM: Artificial Sequence
<220> FEATURE:
<223> OTHER INFORMATION: MF6256

<400> SEQUENCE: 46

```
Glu Val Gln Leu Val Gln Ser Gly Ala Glu Val Lys Lys Pro Gly Ser
1               5                   10                  15

Ser Met Lys Val Ser Cys Lys Ala Ser Gly Gly Thr Phe Ser Ser Tyr
            20                  25                  30

Val Ile Ser Trp Val Arg Gln Ala Pro Gly Gln Gly Leu Glu Trp Met
        35                  40                  45
```

Gly Met Ile Ile Pro Val Phe Asp Thr Ser Ser Tyr Glu Lys Lys Phe
            50                  55                  60

Gln Gly Arg Ile Thr Ile Ile Ala Asp Lys Ser Thr Ser Thr Val Tyr
65                  70                  75                  80

Leu Glu Leu Ser Ser Leu Arg Ser Glu Asp Ala Ala Val Tyr Tyr Cys
                85                  90                  95

Ala Arg Gly Thr Val Glu Ala Thr Leu Leu Phe Asp Phe Trp Gly Gln
                100                 105                 110

Gly Thr Leu Val Thr Val Ser Ser
            115                 120

<210> SEQ ID NO 47
<211> LENGTH: 120
<212> TYPE: PRT
<213> ORGANISM: Artificial Sequence
<220> FEATURE:
<223> OTHER INFORMATION: MF6930

<400> SEQUENCE: 47

Glu Val Gln Leu Val Gln Ser Gly Ala Glu Val Lys Lys Pro Gly Ser
1               5                   10                  15

Ser Met Lys Val Ser Cys Lys Ala Ser Gly Gly Thr Phe Ser Asn Tyr
                20                  25                  30

Val Ile Ser Trp Val Arg Gln Ala Pro Gly Gln Gly Leu Glu Trp Met
            35                  40                  45

Gly Met Ile Ile Pro Val Phe Glu Thr Ala Thr Tyr Glu Lys Lys Phe
            50                  55                  60

Gln Gly Arg Val Thr Ile Ala Asp Lys Ser Thr Ser Thr Val Tyr
65                  70                  75                  80

Met Glu Leu Ser Ser Leu Arg Ser Glu Asp Ala Ala Val Tyr Tyr Cys
                85                  90                  95

Ala Arg Gly Thr Val Glu Ala Thr Leu Leu Phe Asp Tyr Trp Gly Gln
                100                 105                 110

Gly Thr Leu Val Thr Val Ser Ser
            115                 120

<210> SEQ ID NO 48
<211> LENGTH: 120
<212> TYPE: PRT
<213> ORGANISM: Artificial Sequence
<220> FEATURE:
<223> OTHER INFORMATION: MF6932

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Met Ile Ile Pro Phe Phe Asp Thr Ala Asn Tyr Ala Gln Lys Phe
            50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Val Tyr Tyr Cys
                85                  90                  95

Ala Arg Gly Thr Val Ser Ala Thr Leu Val Phe Asp Tyr Trp Gly Gln
                100                 105                 110

```
Gly Thr Leu Val Thr Val Ser Ser
        115                 120

<210> SEQ ID NO 49
<211> LENGTH: 120
<212> TYPE: PRT
<213> ORGANISM: Artificial Sequence
<220> FEATURE:
<223> OTHER INFORMATION: MF6935

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Val Ile Ser Trp Val Arg Gln Ala Pro Gly Gln Gly Leu Glu Trp Met
        35                  40                  45

Gly Met Ile Ile Pro Ile Phe Asp Thr Ala Asn Tyr Ala Gln Lys Phe
    50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Val Tyr Tyr Cys
                85                  90                  95

Ala Arg Gly Thr Val Ser Gly Thr Leu Val Phe Asp Tyr Trp Gly Gln
            100                 105                 110

Gly Thr Leu Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: MF6936

<400> SEQUENCE: 50

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Val Ile Asn Trp Val Arg Gln Ala Pro Gly Gln Gly Leu Glu Trp Met
        35                  40                  45

Gly Met Ile Ile Pro Val Phe Asp Thr Thr Ser Tyr Glu Arg Lys Phe
    50                  55                  60

Gln Gly Arg Val Thr Ile Thr Ala Asp Lys Ser Thr Ser Thr Ala Tyr
65                  70                  75                  80

Met Glu Leu Thr Ser Leu Arg Ser Glu Asp Thr Ala Val Tyr Tyr Cys
                85                  90                  95

Ala Arg Gly Thr Val Gly Ala Thr Leu Leu Phe Asp Asn Trp Gly Gln
            100                 105                 110

Gly Thr Leu Val Thr Val Ser Ser
        115                 120

<210> SEQ ID NO 51
<211> LENGTH: 121
<212> TYPE: PRT
<213> ORGANISM: Artificial Sequence
<220> FEATURE:
<223> OTHER INFORMATION: MF6972
```

<400> SEQUENCE: 51

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Phe Trp Ser Trp Ile Arg Gln Pro Pro Gly Lys Gly Leu Glu Trp Ile
        35                  40                  45

Gly Tyr Ile Ile Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Ser Gly Tyr Gly Asp Asp Phe Asp Ile Trp Gly
            100                 105                 110

Gln Gly Thr Met Val Thr Val Ser Ser
        115                 120

<210> SEQ ID NO 52
<211> LENGTH: 118
<212> TYPE: PRT
<213> ORGANISM: Artificial Sequence
<220> FEATURE:
<223> OTHER INFORMATION: MF6974

<400> SEQUENCE: 52

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Thr Ile Ser Gly Gly Gly Ala Asn Ile Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Phe Cys
                85                  90                  95

Ala Ser Pro Tyr Gly Ser Gly Tyr Phe Asp Val Trp Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: MF6982

<400> SEQUENCE: 53

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Thr Ile Ser Gly Gly Thr Asn Ile Tyr Tyr Ala Asp Ser Val
        50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Gly Asp Thr Ala Val Tyr Tyr Cys
                 85                  90                  95

Ala Ser Pro Tyr Gly Ser Gly Tyr Leu Asp Val Trp Gly Gln Gly Thr
                100                 105                 110

Leu Val Thr Val Ser Ser
            115

<210> SEQ ID NO 54
<211> LENGTH: 119
<212> TYPE: PRT
<213> ORGANISM: Artificial Sequence
<220> FEATURE:
<223> OTHER INFORMATION: MF7676

<400> SEQUENCE: 54

Gln Ile Thr Leu Lys Glu Ser Gly Pro Thr Leu Val Lys Pro Thr Gln
 1                5                 10                  15

Thr Leu Thr Leu Thr Cys Thr Phe Ser Gly Phe Ser Leu Ser Thr Ser
                 20                  25                  30

Lys Val Gly Val Gly Trp Ile Arg Gln Pro Pro Gly Lys Ala Leu Glu
             35                  40                  45

Trp Leu Ala Leu Ile Tyr Trp Asn Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg Arg Gly Trp Gly Pro Phe Asp Tyr Trp Gly Gln Gly
                100                 105                 110

Thr Leu Val Thr Val Ser Ser
            115

<210> SEQ ID NO 55
<211> LENGTH: 119
<212> TYPE: PRT
<213> ORGANISM: Artificial Sequence
<220> FEATURE:
<223> OTHER INFORMATION: MF7677

<400> SEQUENCE: 55

Gln Ile Thr Leu Lys Glu Ser Gly Pro Thr Leu Val Lys Pro Thr Gln
 1                5                 10                  15

Thr Leu Thr Leu Thr Cys Thr Phe Ser Gly Phe Ser Leu Ser Thr Ser
                 20                  25                  30

Gly Val Gly Val Gly Trp Ile Arg Gln Pro Pro Gly Lys Ala Leu Glu
             35                  40                  45

Trp Leu Ala Phe Ile Tyr Ser Asn Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Thr His Arg Arg Gly Trp Gly Pro Phe Asp Tyr Trp Gly Gln Gly
```

-continued

```
                  100                 105                 110

Thr Leu Val Thr Val Ser Ser
            115

<210> SEQ ID NO 56
<211> LENGTH: 119
<212> TYPE: PRT
<213> ORGANISM: Artificial Sequence
<220> FEATURE:
<223> OTHER INFORMATION: MF7678

<400> SEQUENCE: 56

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Val Phe Ile Tyr Ser Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Gly Trp Gly Pro Phe Asp Tyr Trp Gly Gln Gly
            100                 105                 110

Thr Leu Val Thr Val Ser Ser
            115

<210> SEQ ID NO 57
<211> LENGTH: 119
<212> TYPE: PRT
<213> ORGANISM: Artificial Sequence
<220> FEATURE:
<223> OTHER INFORMATION: MF7679

<400> SEQUENCE: 57

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Gly Trp Gly Pro Phe Asp Tyr Trp Gly Gln Gly
            100                 105                 110

Thr Leu Val Thr Val Ser Ser
            115

<210> SEQ ID NO 58
<211> LENGTH: 127
<212> TYPE: PRT
<213> ORGANISM: Artificial Sequence
<220> FEATURE:
```

```
<223> OTHER INFORMATION: teatnus toxin specific VH gene

<400> SEQUENCE: 58

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
            115                 120                 125

<210> SEQ ID NO 59
<211> LENGTH: 6
<212> TYPE: PRT
<213> ORGANISM: Artificial Sequence
<220> FEATURE:
<223> OTHER INFORMATION: VL CDR1

<400> SEQUENCE: 59

Gln Ser Ile Ser Ser Tyr
1               5

<210> SEQ ID NO 60
<211> LENGTH: 9
<212> TYPE: PRT
<213> ORGANISM: Artificial Sequence
<220> FEATURE:
<223> OTHER INFORMATION: VL CDR3

<400> SEQUENCE: 60

Gln Gln Ser Tyr Ser Thr Pro Pro Thr
1               5
```